(12) United States Patent
Papke et al.

(10) Patent No.: US 8,980,923 B2
(45) Date of Patent: Mar. 17, 2015

(54) COMPOSITIONS AND METHODS FOR SELECTIVE INHIBITION OF NICOTINE ACETYLCHOLINE RECEPTORS

(75) Inventors: Roger L. Papke, Gainesville, FL (US); Nicole A. Horenstein, Gainesville, FL (US); Michael M. Francis, Salt Lake City, UT (US); Kyung Il Choi, Seoul (KR)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 13/526,076

(22) Filed: Jun. 18, 2012

(65) Prior Publication Data

US 2012/0329783 A1  Dec. 27, 2012

Related U.S. Application Data

(60) Continuation of application No. 12/264,768, filed on Nov. 4, 2008, now abandoned, which is a division of application No. 10/956,957, filed on Sep. 30, 2004, now Pat. No. 7,531,555.

(60) Provisional application No. 60/507,744, filed on Oct. 1, 2003.

(51) Int. Cl.
*A61K 31/4465* (2006.01)
*C07D 211/44* (2006.01)

(52) U.S. Cl.
CPC ................................. *C07D 211/44* (2013.01)
USPC .......................................... 514/327; 546/242

(58) Field of Classification Search
CPC ..................................................... C07D 211/44
USPC ........................................... 514/327; 546/242
See application file for complete search history.

(56) References Cited

U.S. PATENT DOCUMENTS

| | | | |
|---|---|---|---|
| 3,684,765 A | 8/1972 | Matsui et al. | |
| 4,405,736 A | 9/1983 | Kubota et al. | |
| 4,619,958 A | 10/1986 | Haruna et al. | |
| 4,692,485 A | 9/1987 | Leistner et al. | |
| 5,194,466 A | 3/1993 | Borzatta et al. | |
| 5,290,789 A | 3/1994 | DeHaven-Hudkins et al. | |
| 6,034,079 A * | 3/2000 | Sanberg et al. | 514/225.8 |
| 6,362,009 B1 | 3/2002 | Munoz et al. | |

FOREIGN PATENT DOCUMENTS

| | | |
|---|---|---|
| DE | 38 44 356 A1 | 5/1990 |
| EP | 0 275 696 B1 | 4/1992 |
| EP | 0 427 672 B1 | 9/1993 |
| EP | 0 505 465 B1 | 3/1996 |
| EP | 0 558 487 B1 | 10/1998 |
| WO | WO 94/07489 A1 | 4/1994 |
| WO | WO 01/98266 A2 | 12/2001 |

OTHER PUBLICATIONS

Wikipedia "Nicotine antagonist" p. 1 (2012).*
J. European Psychiatry, editors p. 1 (2013) from internet.*
Marzurov et al. "Novel nicotoinic . . ." Bioorg. Med. Chemm. Lett. v.23, p. 3972-3934 (2013).*
Peng et al. "Chronic nicotine . . ." Am. Soc. Pharma. Exp. Ther. v. 51, p. 776-784 (1997).*
Sano "clinical trial prress release" p. 1 (1997).*
Howson et al. "Clinical and attentional . . ." Eur. Psychiary v.19, p. 102-112 (2004).*
Nicotine agonist, Wikipedia, p. 1-7 (2013).*
Rose et al. "Nicotine/,ecamuylamine . . ." Dryg. Dev. Res. v.38, p. 243-256 (1996).*
Sanberg et al. "Treatment of Tourette's . . ." Lancet v. 352 No. 9129 p. 1-3 (1998).*
Spinks et al. "Polyalkyl piperidines . . ." Nature, No. 4620, May 17,p. 1397-1398 (1958).*
Transdermal patch, Wikipedia, p. 1-4 (2013).*
Spink et al. "The pharmacological . . ." Br. J. Pharmacol. v.13, p. 501-520 (1958).*
Sanberg et al. "Nicotine for the treatment . . ." Pharmacol. Ther. v. 74, p. 21-25 (1997).*
Decker et al. "Therapeutic potential of . . ." Bhichem. Pharm. v/58, p. 917-923 (1999).*
Kenneth et al. "Neuronal nicotinic . . ." J. PHar. Exp. Ther. v. 292(2) 461-467 (2000).*
Pugh "How does nicotine act?" Galaxygoo.org p. 1-4 (2002).*
Schwabe et al. "Treating tourettes . . ." Wis. Med. J. 88(10) 23-27. abstract (1989).*
Silver et al. "Transdemal nicotine and haloperidol . . ." J. Clin. Psy. 62(9) 707-14, abstract (2001).*
Benowitz, N.L. "Pharmacology of nicotine: Addiction and therapeutics" *Annu. Rev. Pharm. Toxicol.*, 1996, 36:597-613.
Buznikov, G.A. et al. "Nicotinic antagonists (piperidines and quinuclidines) reduce the susceptibility of early sea urchin embryos to agents evoking calcium shock" *Gen. Pharmac.*, 1997, 29(1):49-53.

(Continued)

*Primary Examiner* — Celia Chang
(74) *Attorney, Agent, or Firm* — Saliwanchik, Lloyd & Eisenschenk

(57) ABSTRACT

The present invention concerns methods for treating or preventing neurological disorders characterized by dysfunction of nicotinic acetylcholine receptors by administering 2,2,6,6-tetramethylpiperidin-4-yl heptanoate (TMPH), or a pharmaceutically acceptable salt thereof, to the patient. In another aspect, the present invention pertains to pharmaceutical compositions containing TMPH, or a pharmaceutically acceptable salt thereof, and a pharmaceutically acceptable carrier. In another aspect, the present invention pertains to methods for selectively inhibiting nicotinic acetylcholine receptors that lack an α5, α6, or β3 subunit by contacting an effective amount of TMPH, or a pharmaceutically acceptable salt thereof, to the receptor. The method for selectively inhibiting nicotinic acetylcholine receptors that lack an α5 subunit can be carried out in vivo or in vitro.

14 Claims, 24 Drawing Sheets

(56) References Cited

OTHER PUBLICATIONS

Cooper, E.C. and Jan, L.Y. "Ion channel genes and human neurological disease: Recent progress, prospects, and challenges" *Proc. Natl. Acad. Sci. USA,* 1999, 96:4759-4766.

Cordero-Erausquin, M. and Changeux, J-P. "Tonic nicotinic modulation of serotoninergic transmission in the spinal cord" *PNAS,* 2001, 98(5):2803-2807.

Damaj, M.I. et al. "Antinociceptive responses to nicotinic acetylcholine receptor ligands after systemic and intrathecal administration in mice" *J Pharmacol Exp Ther,* 1998, 284:1058-1065.

Damiani, E. et al. "The effects of nitroxide radicals on oxidative DNA damage" *Free Radic. Biol. Med.,* 2000, 28(8):1257-1265.

Francis, M.M. "Subunit-Specific Determinants of Function and Pharmacology of Nicotinic Acetylcholine Receptors", Doctoral Dissertation, University of Florida, 1998.

Francis, M.M. et al. "Sensitivity to voltage-independent inhibition determined by pore-lining region of the acetylcholine receptor" *Biophys. J.,* 1998, 74(5):2306-2317.

Francis, M.M. and Papke, R.L. "Muscle-type nicotinic acetylcholine receptor delta subunit determines sensitivity to noncompetitive inhibitors, while gamma subunit regulates divalent permeability" *Neuropharmacology,* 1996, 35(11):1547-1556.

Freedman, R. et al. "The alpha7-nicotinic acetylcholine receptor and the pathology of hippocampal interneurons in schizophrenia" *J. Chem. Neuroanatomy,* 2000, 20:299-306, abstract.

Freedman, R. et al. "Schizophrenia and nicotinic receptors" *Harvard Rev. Psych.,* 1994, 2:179-192, abstract.

Garcia-Colunga, J. and Miledi, R. "Effects of serotonergic agents on neuronal nicotinic acetylcholine receptors" *Proc. Natl. Acad. Sci. USA,* 1995, 92:2919-2923.

Glossmann, H. et al. "A light stabilizer (Tinuvin 770) that elutes from polypropylene plastic tubes is a potent L-type $Ca^{2+}$-channel blocker" *Proc. Natl. Acad. Sci. USA,* 1993, 90:9523-9527.

Graham, J.H. et al. "Potential Central Activity of Tinuvin, a Novel Nicotinic Receptor Antagonist", 2001, abstract, vol. 27, No. 1, p. 1282, Society for Neuroscience Abstracts, presented at the 31st annual Meeting of the Society for Neuroscience, Bristol, TN, Nov. 10-15, 2001.

Hollady, M.W. et al. "Neuronal nicotinic acetylcholine receptors as targets for drug discovery" *J. Med. Chem.,* 1997, 40:4169-4194.

Jackson-Lewis, V. and Liberatore, G. "Effects of a unilateral stereotaxic injection of Tinuvin 123 into the substantia nigra on the nigrostriatal dopaminergic pathway in the rat" *Brain Res.,* 2000, 866(1-2):197-210.

Kurenny, D.E. et al. "Mechanism of long-lasting block of ganglion nicotinic receptors by mono-ammonium compounds with long aliphatic chain" *J. Auton. Nerv. Syst.,* 1994, 48(3):231-240.

Latoxan web page (www.latoxan.com), published Nov. 2002 or earlier.

Lloyd, G.K. and Williams, M. "Neuronal nicotinic acetylcholine receptors as novel drug targets" *J. Pharm. Exp. Therapies,* 2000, 292(2):461-467.

Marubio, L.M. et al. "Effects of nicotine in the dopaminergic system of mice lacking the alpha4 subunit of neuronal nicotinic acetylcholine receptors" *Eur J Neurosci,* 2003, 17:1329-1337.

Meyer, E.M. et al. "Neuroprotective and memory-related actions of novel alpha-7 nicotinic agents with different mixed agonist/antagonist properties" *J. Pharmacology Exp. Therap.,* 1998, 284(3):1026-1032.

Mihailescu, S. and Drucker-Colin, R. "Nicotine, brain nicotine receptors, and neuropsychiatric disorders" *Arch. Med. Res.,* 2000, 31:131-144.

Newhouse, P.A. and Kelton, M. "Nicotinic systems in central nervous systems disease: degenerative disorders and beyond" *Pharm. Acta Helv.,* 2000, 74:91-101.

Newhouse, P.A. et al. "Nicotinic system involvement in Alzheimer's and Parkinson's diseases. Implications for therapeutics" *Clin. Pharm.,* 1997, 11:206-228.

Papke, R.L. et al. "In vivo and in vitro characterization of a novel and selective inhibitor of CNS nicotinic receptors" unpublished; publication pending.

Papke, R.L. et al. "In vitro and in vivo characterization of a novel and selective inhibitor of CNS nicotinic receptors" abstract presented at the Society for Neuroscience 2003 annual meeting in New Orleans, Nov. 9, 2003, program No. 158.11.

Papke, R.L. and Papke, J.K. "Comparative pharmacology of rat and human $\alpha 7$ nAChR conducted with net charge analysis" *Br J of Pharmacol,* 2002, 137:49-61.

Papke, R.L. "Enhanced inhibition of a mutant neuronal nicotinic acetylcholine receptor by agonists: protection of function by (E)-N-Methyl-4-(3-pyridinyl)-3-butene-1-amine (TC-2403)" *J. Pharm. Exp. Thera.,* 2002, 301(2):765-773.

Papke, R.L. et al. "Analysis of mecamylamine stereoisomers on human nicotinic receptor subtypes" *J. Pharmacol. Exp. Ther.,* 2001, 297(2):646-656.

Papke, R.L. et al. "$\alpha 7$ receptor-selective agonists and modes of $\alpha 7$ receptor activation" *Euro. J. Pharm.,* 2000, 393:179-195.

Papke, R.L. et al. "The activation and inhibition of human nicotinic acetylcholine receptor by RJR-2403 indicate a selectivity for the $\alpha 4\beta 2$ receptor subtype" *J. Neurochem.,* 2000, 75:204-216.

Papke, R.L. et al. Laboratory web page (www.mbi.ufl.edu/papkelab/struct/ncbfigu.jpg), 1999.

Papke, R.L. et al. "Activation and inhibition of rat neuronal nicotinic receptors by ABT-418" *Brit. J. Pharm.,* 1997, 120:429-438.

Papke, R.L. et al. "Bridging the nicotinic acetylcholine receptor channel: Prologed inhibition associated with use-dependent binding of a bi-functional inhibitor" *Soc. Neurosci. Abst.,* 1994, 20(1-2):1123, abstract, presented at the $24^{th}$ Annual Meeting of the Society for Neuroscience, Nov. 13-18, 1994.

Papke, R.L. et al. "Inhibition of Nicotinic Acetylcholine Receptors by Bis (2,2,6,6,-tetramethyl-4-piperidinyl) sebacate (Tinuvin 770), an Additive to Medical Plastics" *J. Pharmacol. Exp. Ther.,* 1994, 268(2):718-726.

Papke, R.L. et al. "Use-dependent Inhibition of Neuronal Nicotinic ACHR by Tinuvin 770 (Bis(2,2,6,6-tetramethyl-4-piperidinyl) Sebacate), A Possible Additive to Laboratory Plastics", 1993, abstract, vol. 64, No. 2, part 2, p. A323, abstract W-Pos421, Biophysical Journal Abstracts, presented at the 37th Annual meeting of the Biophysical Society, Washington, D.C, Feb. 14-18, 1993.

Papke, R.L. and Heinemann, S. "The role of the $\beta_4$-subunit in determining the kinetic properties of rat neuronal nicotinic acetylcholine $\alpha_3$-receptors" *J. Physiol.* (Lond.), 1991, 440:95-112.

Rao, T.S. et al. "Evaluation of anti-nociceptive effects of neuronal nicotinic acetylcholine receptor (NAChR) ligands in the rat tail-flick assay" *Neuropharmacology,* 1996, 35(4):393-405.

Rose, J.E. et al. "Mecamylamine combined with nicotine skin patch facilitates smoking cessation beyond nicotine patch treatment alone" *Clin. Pharmacol. Ther.,* 1994, 56:86-99.

Salas, R. et al. "The nicotinic acetylcholine receptor subunit $\alpha 5$ mediates short-term effects of nicotine in vivo" *Mol Pharmacol,* 2003, 63:1059-1066.

Sanberg, P.R. et al. "Treatment of Tourette's syndrome with mecamylamine" *Lancet,* 1998, 352:705-706.

Shoaib, M. et al. "The role of nicotinic receptor beta-2 subunits in nicotine discrimination and conditioned taste aversion" *Neuropharmacology,* 2002, 42:530-539.

Sotonyi, P. et al. "A light stabilizer Tinuvin 770-induced toxic injury of adult rat cardiac myocytes" *Forensic. Sci. Int.,* 2001, 119(3):322-327.

Tritto, T. et al. "Null mutant analysis of responses to nicotine: deletion of beta2 nicotinic acetylcholine receptor subunit but not alpha7 subunit reduces sensitivity to nicotine-induced locomotor depression and hypothermia" *Nicotine Tob Res,* 2004, 6:145-158.

Vernallis, A.B. et al. "Neurons assemble acetylcholine receptors with as many as three kinds of subunits while maintaining subunit segregation among receptor subtypes" *Neuron,* 1993, 10:451-464.

Webster, J.C. et al. "Antagonist activities of mecamylamine and nicotine show reciprocal dependence on beta subunit sequence in the second transmembrane domain" *Brit. J. Pharma.,* 1999, 127:1337-1348.

(56) References Cited

OTHER PUBLICATIONS

Xiao, A.Y. et al. "The industrial chemical Tinuvin 123 does not induce dopaminergic neurotoxicity in C57B1/6 mice" *Neurosic. Lett.,* 2000, 278(3):165-168.
Araki, H. et al. "Neuronal nicotinic receptor and psychiatric disorders: functional and behavioral effects of nicotine" *Jpn. J. Pharmacol,* 2002, 88(2):133-138.
Mihailescu, S. and Drucker-Colin, R. "Nicotine and brain disorders" *Acta Pharmacologica Sinica,* 2000, 21(2):97-104.
Nath, S. et al. "Molecular simulation of physical properties of hindered-amine light stabilizers in polyethylene" *J. Am. Chem. Soc.,* 1999, 121:4252-4261.
Wilbraham, A. and Matta, M. "Organic and biological chemistry" Southern Illinois University, 1984, pp. 268-269.
Popik, P. et al. "NMDA antagonist properties of the putative antiaddictive drug, ibogaine" *J. Pharma. Exp. Ther.,* 1995, 275(2):753-760.
Cohen, C. et al. "CB1 receptor antagonists for the treatment of nicotine addiction" *Pharma., Biochem. Behav.,* 2005, 81(2):387-395.
Betz, H. "Characterization of the α-bungarotoxin receptor in chick-embryo retina" *Eur. J. Biochem.,* 1981, 117:131-139.
Oz, M. et al. "Differential effects of endogenous and synthetic cannabinoids on alpha SUB 7-nicotinic acetylcholine receptor-mediated responses in *Xenopus* oocytes" *J Pharmacol. Exp. Ther.,* 2004, 310:1152-1160.
Silvia, D. et al. "Molecular biology and electrophysiology of neuronal nicotinic receptors of rat chromaffin cells" *Eur. J. Neurosci.,* 2003, 17(11):2313-2322.
CA RN 60-40-2 Mecamylamine (1967).
Gaevoi et al. "Kinetic characteristics of the associative interactions of nitroxyl radicals with micelles of anion-active surfactant compounds" CA111:181306, 1989.
Zakrzewski "A reaction of nitroxides with ethyl mercaptan. A mild method for the conversion of nitroxides into their corresponding amines" CA114:42528, 1991.

\* cited by examiner

COMPOSITIONS AND METHODS FOR SELECTIVE INHIBITION OF NICOTINE ACETYLCHOLINE RECEPTORS

CROSS-REFERENCE TO RELATED APPLICATIONS

This application is a continuation of U.S. application Ser. No. 12/264,768, filed Nov. 4, 2008, now abandoned, which is a divisional of U.S. application Ser. No. 10/956,957, filed Sep. 30, 2004, now U.S. Pat. No. 7,531,555, which claims benefit of U.S. Provisional Application Ser. No. 60/507,744, filed Oct. 1, 2003, each of which is hereby incorporated by reference herein in its entirety, including any figures, tables, nucleic acid sequences, amino acid sequences, and drawings.

GOVERNMENT SUPPORT

The subject invention was made with government support under a research project supported by National Institutes of Health Grant NS32888 and National Institutes of Mental Health Grant MH11258. Accordingly, the government has certain rights in this invention.

BACKGROUND OF INVENTION

There are multiple types of nicotine acetylcholine receptors (nAChR) in the brain associated with synaptic function, signal processing, or cell survival. The therapeutic targeting of nicotinic receptors in the brain will benefit from the identification of drugs which may be selective for their ability to activate or inhibit a limited range of these receptor subtypes. Mecamylamine is a ganglionic blocker developed many years ago as an antihypertensive and more recently suggested to be useful as a component in the pharmacotherapy for Tourette's syndrome (Sanberg, P. R. et al., *Lancet*, 1998, 352:705-706) and smoking cessation (Rose, J. E. et al., *Clin. Pharmacol. Ther.*, 1994, 56(1):86-99). However, electrophysiological characterization of mecamylamine has shown it to be relatively nonselective (Papke, R. L. et al., *J Pharmacol Exp Ther*, 2001, 297(2):646-56), consistent with the observation that it effectively blocks all of the peripheral and central nervous system (CNS) effects of nicotine (Martin, B. R. et al., *Med. Chem. Res.*, 1993, 2:564-577).

A family of bis-tetramethylpiperidine compounds have been identified as inhibitors of neuronal-type nicotinic receptors (Francis, M. M. et al., *Biophys. J.*, 1998, 74(5):2306-2317). The prototype compound in this series is bis-(2,2,6,6-tetramethyl-4-piperidinyl)-sebacate (BTMPS or Tinuvin 770), which produces a readily reversible block of muscle-type nAChR and a nearly irreversible use-dependent, voltage-independent block of neuronal nAChR. The tetramethyl-piperidine groups of BTMPS are sufficient to inhibit nAChR, and the conjugation of two such groups by a long aliphatic chain accounts for both the selectivity and slow reversibility of BTMPS inhibition of neuronal nAChR (Francis, M. M. et al., 1998).

BRIEF SUMMARY OF THE INVENTION

The subject invention concerns methods of treating a patient suffering from a neurological condition, such as Tourette's syndrome or other tic disorders, characterized by the dysfunction of nicotine acetylcholine receptors (nAChRs), by administering 2,2,6,6-tetramethylpiperidin-4-yl heptanoate (also referred to herein as TMPH or compound I), or a pharmaceutically acceptable salt thereof, to the patient. The use of TMPH facilitates the development of therapies for a number of neurological disorders, with improved selectivity for nAChR subtypes.

According to the method of the present invention, TMPH can be administered as an isolated compound, or administered in a pharmaceutically acceptable carrier as a pharmaceutical composition of the subject invention. Optionally, TMPH can be administered with other pharmacologically active agents, such as nicotinic acetylcholine receptor agonists, antagonists, or mixed agonists/antagonists.

In other aspects, the present invention concerns a compound comprising TMPH or a pharmaceutically acceptable salt thereof; and pharmaceutical compositions containing TMPH, or a pharmaceutically acceptable salt thereof, and a pharmaceutically acceptable carrier.

In another aspect, the present invention pertains to methods for selectively inhibiting nicotinic acetylcholine receptors that lack an $\alpha 5$ subunit, an $\alpha 6$ subunit, or $\beta 3$ subunit by contacting an effective amount of TMPH, or a pharmaceutically acceptable salt thereof, to the receptor. For example, neuronal beta subunit-containing receptors without an $\alpha 5$ subunit, $\alpha 6$ subunit, or $\beta 3$ subunit can be inhibited. Receptors such as muscle-type ($\alpha 1 \beta 1 \gamma \delta$) and $\alpha 7$ receptors, can be inhibited. The method can be carried out in vivo or in vitro. For example, an effective amount of TMPH, or a pharmaceutically acceptable salt thereof, can be administered in vivo to a patient in need thereof, in order to treat a neurological condition, such as nicotine addiction. Alternatively, an effective amount of TMPH, or a pharmaceutically acceptable salt thereof, can be contacted in vitro to isolated nicotine acetylcholine receptors that lack an $\alpha 5$, $\alpha 6$, or $\beta 3$ subunit or to cells that naturally or recombinantly express nicotine acetylcholine receptors that lack an $\alpha 5$, $\alpha 6$, or $\beta 3$ subunit.

BRIEF DESCRIPTION OF DRAWINGS

In FIG. 4A, the upper panel shows raw data traces obtained from an oocyte expressing muscle-type $\alpha 1 \beta 1 \epsilon \delta$ subunits to the application of either 10 μM ACh alone (open circles) or the co-application of 10 μM ACh and 300 nM TMPH (arrow). The lower panel is the averaged normalized data (±SEM, n≥4) from oocytes expressing $\alpha 1 \beta 1 \epsilon \delta$ subunits to the co-application 10 μM ACh and a range of TMPH concentrations. In FIG. 4B, the upper panel shows raw data traces obtained from an oocyte expressing ganglionic-type α3β4 subunits to the application of either 100 μM ACh alone (open circles) or the co-application of 100 μM ACh and 300 nM TMPH (arrow). The lower panel is the averaged normalized data (±SEM, n≥4) from oocytes expressing α3β4 subunits to the co-application 100 μM ACh and a range of TMPH concentrations. Three values are plotted in each of the concentration-response curves: (♦) the peak current amplitude of the co-application response, normalized to the peak amplitude of the previous ACh control; (▼) the net charge of the co-application response, normalized to the net charge of the previous ACh control (Papke and Papke, 2002); and (●) the peak current amplitude of the ACh control response obtained after the TMPH/ACh co-application, normalized to the peak amplitude of the previous ACh control.

FIG. 7A contains representative data showing the effects of the application of 1 μM TMPH alone to α4β2 and α3β2 expressing oocytes (open arrows), compared to the application of to ACh alone (open circles) either before or after the application of TMPH. The control ACh concentrations used were 10 μM and 30 μM for α4β2 and α3β2, respectively. FIG. 7B shows comparison of the use-dependent (1 μM TMPH+ACh) and use-independent (1 μM TMPH alone) inhibition of α3β4, α4β2, and α3β2 receptors by TMPH. The data are calculated from the peak amplitudes of control ACh responses obtained after the application of TMPH±ACh, expressed relative to the peak current amplitude of ACh control responses prior to the application of TMPH.

FIG. 8A shows responses of an oocyte expressing α4β2 receptors to alternating applications of 30 μM ACh alone (open circles) or 30 μM ACh plus 100 nM TMPH (arrows). The total inhibition increased during the first 3 TMPH/ACh co-applications. Note that the TMPH/ACh co-applications differ in kinetics from the ACh controls, showing a greater inhibition of net charge than of peak current. FIG. 8B shows normalized average responses of oocytes expressing α4β2 receptors (±SEM, n≥4) to alternating applications of ACh alone or ACh plus TMPH, as in FIG. 8A. Both peak currents and net charge values are plotted, normalized to the ACh control response recorded before the first ACh/TMPH co-application (t=−5 minutes). Note that the traces in FIG. 8A are shown on the same time scale as the X-axis in FIG. 8B.

FIG. 10A shows representative traces obtained from oocytes expressing human α3β2 or α3β2α5 subunits. Following an initial application of ACh alone (open circle), a single co-application was made of ACh and 1 μM TMPH (arrow). Recovery was evaluated by making repeated control ACh applications at 5 minute intervals (open circles). FIG. 10B shows normalized average responses of oocytes expressing α3β2 or α3β2α5 receptors (±SEM, n≥4) to repeated applications of ACh alone, following a single application of ACh plus TMPH (as in FIG. 10A). Peak currents are plotted, normalized to the ACh control response recorded before the ACh/TMPH co-application. Note that the traces in FIG. 10A are shown on the same time scale as the X-axis in FIG. 10B.

DETAILED DISCLOSURE OF THE INVENTION

Figure 1A:
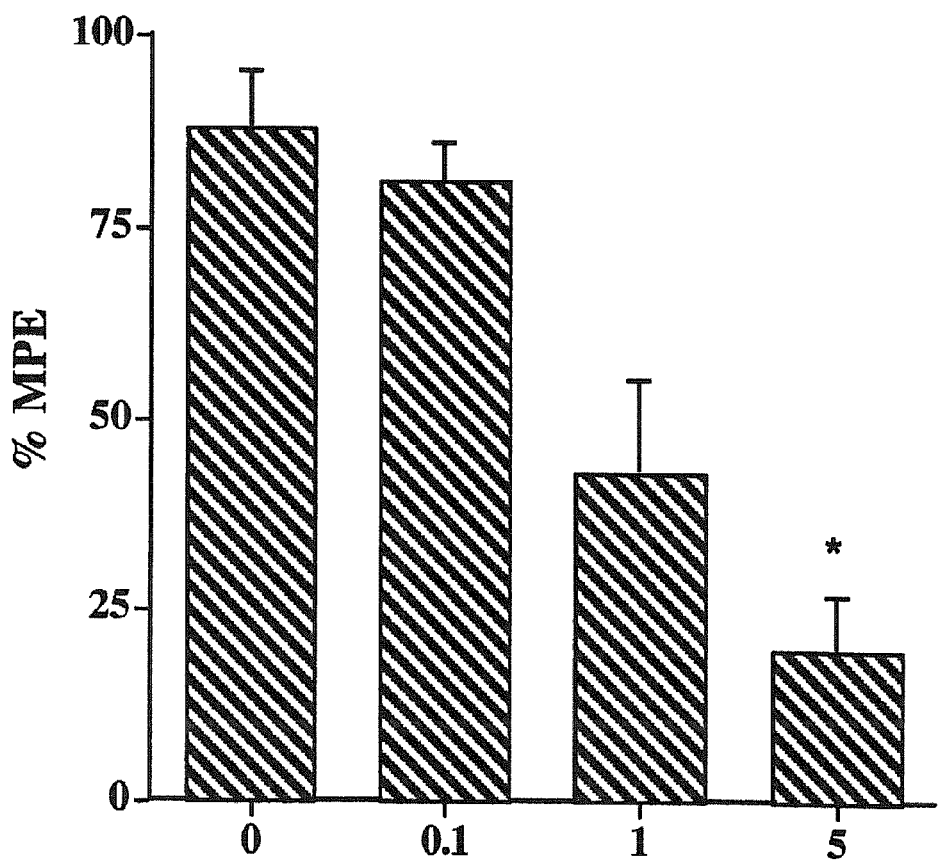
FIGS. 1A-1B show the dose-response blockade of nicotine-induced antinociception in the tail-flick (FIG. 1A) and the hot-plate test (FIG. 1B) by TMPH after s.c. injection in mice. TMPH at different doses was administered s.c. 10 min before nicotine (2.5 mg/kg, s.c.) and mice were tested 5 min later. Each point represents the mean±SE of 8 to 12 mice.

The present inventors have determined that 2,2,6,6-tetramethylpiperidin-4-yl heptanoate (also referred to herein as TMPH or compound I), a compound that has a single tetramethyl-piperidine group and an aliphatic chain, is a potent inhibitor of neuronal nicotinic receptors. Moreover, when delivered systemically, TMPH can block the effects of nicotine on the central nervous system (CNS), indicating that this drug is able to cross the blood-brain barrier and access sites in the brain. Surprisingly, however, unlike the prototype CNS-active nicotinic inhibitor, mecamylamine, TMPH blocks only some of the CNS effects of nicotine, indicating that it has a unique selectivity for specific receptor subtypes in the brain. Since non-selective nicotinic inhibitors with CNS activity have been suggested to be potentially useful treatments for neuropsychiatric disorders and for promoting smoking cessation, a more selective agent, such as TMPH, can provide therapeutic approaches with a reduced range of side effects. Additionally, based on the characterization of this agent's effects on specific nAChR subtypes, TMPH may identify the particular molecular substrates that underlie the multiple effects of nicotine on the brain. TMPH (compound I) is shown below.

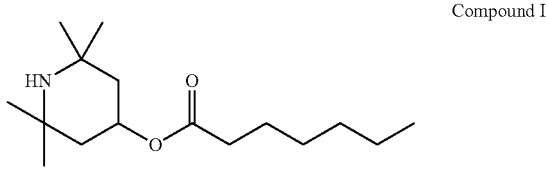 [SMILES: CCCCCCC(=O)OC1CC(C)(C)NC(C)(C)C1]

Compound I

The subject invention concerns methods of treating a patient suffering from a neurological condition characterized by the dysfunction of nicotine acetylcholine receptors (nAChRs) by administering 2,2,6,6-tetramethylpiperidin-4-yl heptanoate (also referred to herein as TMPH or compound I), or a pharmaceutically acceptable salt thereof, to the patient.

The fact that nAChRs having an α5, α6, or β3 subunit are spared from the inhibitory effects of TMPH permits the tuning of the selectivity of specific compounds to increase desired effects and diminish side effects. For example, the selective inhibition of nAChRs lacking an α5, α6, or β3 subunit by administration of TMPH, or a pharmaceutically acceptable salt thereof, permits the avoidance of side effects (e.g., increased heart rate and increased blood pressure) normally associated with the inhibition of nAChRs containing these subunits by non-selective inhibitors, such as Tinuvin 770 and mecamylamine. As used herein, the terms α5, α6, and β3 subunits include the human nicotinic acetylcholine receptor subunits and mammalian homologs of the same name (Chini et al., *Proc. Natl. Acad. Sci. USA* 89:1572-1576).

Preferably, the compounds (TMPH, or a pharmaceutically acceptable salt thereof) and compositions of the subject invention are administered to treat a patient suffering from a neurological disorder associated with dysfunction of one or more subtypes of nAChR, or to prevent onset of the disorder. Neurological disorders which can be treated or prevented with pharmaceutical compositions of the present invention, and in accordance with methods of the present invention, include, but are not limited to, Tourette's syndrome or other tic disorders, presenile dementia (early onset Alzheimer's disease), senile dementia (dementia of the Alzheimer's type), Parkinsonism including Parkinson's disease, Huntington's chorea, tardive dyskinesia, hyperkinesias, mania, attention deficit disorder, attention deficit hyperactivity disorder, sleep-wake disorder, chronic-fatigue syndrome, tremor, epilepsy, neuropathic pain, addiction (e.g., nicotine/smoking addiction), anxiety, dyslexia, schizophrenia, and obsessive-compulsive disorder (Salamone, F. et al., *MJM*, 2000, 5:90-97; Cooper, E. C. and Jan, L. Y. *Proc. Natl. Acad. Sci. USA*, 1999, 96:4759-4766; Sharples, C. and Wonnacott, S, *Neuronal Nicotinic Receptors*, October 2001, 19:1-12; Mihailescu, S, and Drucker-Colin, R. *Arch. Med. Res.*, 2000, 31:131-144; Papke, R. L. et al., *Euro. J. Pharm.*, 2000, 393: 179-195; Newhouse, P. A. and Kelton, M. *Pharm. Acta Helv.*, 2000, 74:91-101; Newhouse, P. A. et al., *Clin. Pharm.*, 1997, 11:206-228; Lloyd, G. K. and Williams, M. *J. Pharm. Exp. Therapies*, 2000, 292:461-467; Hollady, M. W. et al., *J. Med. Chem.*, 1997, 40:4169-4194; Benowitz, N. L. *Annu. Rev. Pharm. Toxicol.*, 1996, 36:597-613; Freedman, R. et al., *Harvard Rev. Psych.*, 1994, 2:179-192; and Freedman, R. et al., *J. Chem. Neuroanatomy*, 2000, 20:299-306).

In a specific embodiment, the method of the present invention involves administration of TMPH, or a pharmaceutically acceptable salt thereof, to a patient as adjunctive therapy in order to treat or prevent Tourette syndrome (TS) or other tic disorder, such as transient or chronic tic disorders. As described in *A Physician's Guide to Diagnosis and Treatment of Tourette Syndrome* (published by the Tourette Syndrome Association, Inc., 1984), TS is characterized by multiform, frequently changing motor and phonic tics. The prevailing diagnostic criteria include onset before the age of 21; recurrent, involuntary, rapid, purposeless motor movements affecting multiple muscle groups; one or more vocal tics; variations in the intensity of the symptoms over weeks to months (waxing and waning); and a duration of more than one year. Of course, these criteria are not absolute. The varied symptoms of TS can be divided into motor, vocal, and behavioral manifestations. Motor symptoms can include simple motor tics, which are fast, darting, and meaningless, and complex motor tics, which are slower, may appear purposeful (includes copropraxia and echopraxia). Vocal symptoms can include simple vocal tics, which are meaningless sounds and noises, and complex vocal tics, which are linguistically meaningful utterances, such as words and phrases (including coprolalia, echolalia, and palilalia). Behavior and developmental symptoms can include attention deficit hyperactivity disorder, obsessions and compulsions, emotional lability, irritability, impulsivity, aggressivity, self-injurious behaviors, and varied learning disabilities. The methods and compositions of the present invention can be used to prevent or lessen the severity of one or more of these symptoms. Preferably, the methods and compositions of the present invention are used as an adjunctive therapy in combination with other pharmacologic treatments for TS, such as haloperidol (HALDOL), pimozide (ORAP) or other neuroleptics, clonidine (CATAPRESE), clomipramine, fluoxetine (PROZAC), and combinations thereof. For example, compositions containing TMPH, or a pharmaceutically acceptable salt thereof, and one or more of the aforementioned drugs are encompassed by the invention and may be administered in accordance with the methods of the invention.

In another embodiment of the method of the present invention, TMPH or a pharmaceutically acceptable salt thereof, is administered to a patient for treatment or prevention of nicotine addition. TMPH or a pharmaceutically acceptable salt thereof can be administered with another pharmacologically active compound to treat or prevent nicotine addiction. For example, TMPH or a pharmaceutically acceptable salt thereof can be administered to a patient in combination with nicotine (e.g., nicotine can be transdermally administered by application of a nicotine patch).

Mammalian species which benefit from the disclosed methods of treatment include, and are not limited to, apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. The term "patient" is intended to include such human and non-human mammalian species.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations containing pharmaceutically acceptable carriers are described in a number of sources which are well known and readily available to those skilled in the art. For example, Remington's Pharmaceutical Sciences (Martin E W, Remington's Pharmaceutical Sciences, Easton Pa., Mack Publishing Company, $19^{th}$ ed., 1995) describes formulations that can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

The TMPH or pharmaceutically acceptable salt thereof can be produced by methods known in the art for synthesis of hindered amine compounds.

TMPH, or a pharmaceutically acceptable salt thereof (or a pharmaceutical compositions containing TMPH or a pharmaceutically acceptable salt thereof), can be administered to a patient by any route that results in prevention or alleviation of symptoms associated with the particular neurological condition. For example, as described in more detail below, TMPH or a pharmaceutically acceptable salt thereof can be administered parenterally, intravenously (I.V.), intramuscularly (I.M.), subcutaneously (S.C.), intradermally (I.D.), orally, intranasally, etc. Examples of intranasal administration can be by means of a spray, drops, powder or gel. However, other means of drug administrations are well within the scope of the present invention.

The pharmaceutical compositions disclosed herein may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, TMPH or a pharmaceutically acceptable salt thereof may be incorporated into sustained-release preparation and formulations.

TMPH may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases of injection, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils.

The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating TMPH, or a pharmaceutically acceptable salt thereof, in the required amount in the appropriate solvent with other various ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Examples of "pharmaceutically acceptable carriers" include any and all solvents, dispersion media, coatings, antibacterial and antifungal agents, isotonic and absorption delaying agents and the like. The use of such media and agents for pharmaceutical active substances is well known in the art. In one embodiment, the pharmaceutically acceptable carrier is a sterile, fluid (e.g., liquid or gas) preparation rendering the pharmaceutical composition suitable for injection or inhalation. Except insofar as any conventional media or agent is incompatible with the active ingredient, its use in the therapeutic compositions is contemplated. Supplementary active ingredients can also be incorporated into the compositions.

For oral prophylaxis, TMPH or a pharmaceutically acceptable salt thereof, may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, TMPH or a pharmaceutically acceptable salt thereof, may be incorporated into an antiseptic wash containing sodium borate, glycerin and potassium bicarbonate. TMPH or a pharmaceutically acceptable salt thereof may also be dispersed in dentifrices, including: gels, pastes, powders and slurries. TMPH or a pharmaceutically acceptable salt thereof may be added in a therapeutically effective amount to a paste dentifrice that may include water, binders, abrasives, flavoring agents, foaming agents, and humectants.

The phrase "pharmaceutically acceptable" refers to molecular entities and compositions that do not produce an allergic or similar untoward reaction when administered to a human. The preparation of an aqueous composition that contains an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition of the present invention can be formulated in a neutral or salt form. Pharmaceutically-acceptable salts, include the acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage foiins such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, *Remington's Pharmaceutical Sciences*). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

According to the therapeutic methods of the present invention, TMPH, or a pharmaceutically acceptable salt thereof, is administered (brought into contact with nAChRs lacking $\alpha 5$, $\alpha 6$, or $\beta 3$ subunits in vivo) and dosed in accordance with good medical practice, taking into account the clinical condition of the individual patient, the site and method of administration, scheduling of administration, patient age, sex, body weight, and other factors known to medical practitioners. The pharmaceutically "effective amount" for purposes herein is thus determined by such considerations as are known in the art. For therapeutic methods, the amount of TMPH, or a pharmaceutically acceptable salt thereof, must be effective to achieve improvement including but not limited to total prevention and to improved survival rate or more rapid recovery, or improvement or elimination of symptoms associated with the particular neurological condition, such as Tourette's syndrome or other tic disorders, and other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration. Optionally, the therapeutic methods of the invention further comprise diagnosis of the patient with a neurological condition by a medical practitioner (e.g., a medical doctor, veterinarian, or other clinician). The therapeutic methods may further comprise evaluating the patient for one or more symptoms associated with the neurological condition before and/or after administration of TMPH or a pharmaceutically acceptable salt thereof.

The methods and compositions of the invention may incorporate additional pharmacologically active agents (such as for adjunctive therapy), in addition to TMPH or a pharmaceutically acceptable salt thereof. For example, the additional pharmacologically active agent can be co-administered consecutively or simultaneously (e.g., in the same formulation or different formulations.

In one embodiment, the additional pharmacologically active agent is an nAChR modulator, such as an inhibitor of nAChR activity. Preferably, the agent is a selective inhibitor. In one embodiment, the agent is a TMPH-related compound, its structure differing from TMPH in having a single tetramethyl piperidine group and an aliphatic chain that is either longer or shorter than that of TMPH (e.g., having a hydrocarbon length of 1, 2, 3, 4, 5, 7, 8, 9, 10, 11, 12, 13, 14, 15 ... etc.).

As used herein, the term "treatment" or grammatical variations thereof is intended to mean reducing (e.g., lessening or eliminating) or preventing of one or more symptoms associated with a particular neurological disorder characterized by dysfunction (e.g., overactivation or overexpression) of one or more subtypes of nAChR.

As used herein, "activity" of a nAChR refers to any activity characteristic of a nAChR. Such activity can typically be measured by one or more in vitro methods, and frequently corresponds to an in vivo activity of a nAChR. Thus, the terms "function" and "activity" with respect to nicotine AChR means that the receptor channel is able to provide for and regulate entry of nicotinic AChR-permeable ions, such as, for example, $Na^+$, $K^+$, $Ca^{2+}$, or $Ba^{2+}$, in response to a stimulus and/or bind ligands with affinity for the receptor. Preferably, such nicotinic AChR activity is distinguishable, such as by electrophysiological, pharmacological, and other means known to those of skill in the art, from the endogenous nicotinic AChR activity that may be produced by the host cell in the absence of TMPH or a pharmaceutically acceptable salt thereof. As used herein, the term "inhibit" with respect to nAChR activity is intended to include partial or complete inhibition of nAChR activity.

In another aspect, the present invention pertains to methods for selectively inhibiting nicotinic acetylcholine receptors that lack an α5, α6, or β3 subunit by contacting an effective amount of TMPH, or a pharmaceutically acceptable salt thereof, to the receptor or combination of receptor subunits in vitro or in vivo. For example, neuronal beta subunit-containing receptors lacking an α5, α6, or β3 subunit can be inhibited. Receptors such as muscle-type (α1β1γδ), and α7 receptors, can be inhibited. The method can be carried out in vivo or in vitro. For example, an effective amount of TMPH, or a pharmaceutically acceptable salt thereof, can be administered in vivo to a patient in need thereof. Alternatively, an effective amount of TMPH, or a pharmaceutically acceptable salt thereof, can be contacted in vitro to nicotine acetylcholine receptors that lack an α5, α6, or β3 subunit or to cells that naturally or recombinantly express nicotine acetylcholine receptors that lack an α5, α6, or β3 subunit. Optionally, the method further comprises determining nAChR activity before, during, or after the TMPH or a pharmaceutically acceptable salt thereof is contacted with the nAChR subunit(s). The effect of TMPH or a pharmaceutically acceptable salt thereof on a particular nAChR subunit combination can be determined by comparison of the change in receptor function (e.g., by electrophysiological recordings). The nAChR subunits can be mammalian, such as human. Examples of host cells appropriate for recombinant expression of neuronal nAChR subunits include, but are not limited to, bacterial cells (e.g., *Escherichia coli*), yeast cells (e.g., methylotrophic yeast cells, such as *Pichia pastoris*), and mammalian cells (e.g., HEK 293, CHO and Ltk⁻ cells). The cells to which TMPH or a pharmaceutically acceptable salt thereof may be contacted in vitro include isolated cells, cell cultures, cell lines, tissues (e.g., tissue cultures), etc.

In other preferred embodiments, eukaryotic cells which contain heterologous nucleic acid sequences encoding nicotinic AChR(s) express the heterologous nucleic acid sequences and form recombinant functional nicotinic AChR(s). In more preferred aspects, recombinant nicotinic AChR activity is readily detectable because it is a type that is absent from the untransfected host cell or is of a magnitude not exhibited in the untransfected cell. Such cells that contain recombinant receptors can be prepared, for example, by causing cells transformed with DNA encoding nicotinic AChR $α_3$ and $β_4$ subunits to express the corresponding proteins. The resulting synthetic or recombinant receptor would contain only the $α_3$ and $β_4$ nAChR subunits. Testing of single receptor subunits with TMPH, or a pharmaceutically acceptable salt thereof, can provide additional information with respect to the function and activity of the individual subunits in response to this selective inhibitor. Such information may lead to the identification of other compounds which are capable of very specific interaction with one or more of the receptor subunits. Such specificity may prove of great value in medical application.

Thus, nucleic acid sequences encoding one or more nicotinic AChR subunits (e.g., human nicotinic AChR subunits) may be introduced into suitable host cells (e.g., eukaryotic or prokaryotic cells) for expression of individual subunits and functional AChRs. Preferably, combinations of alpha and beta subunits may be introduced into cells. Such combinations include any combinations of any one or more of $α_1$, $α_2$, $α_3$, $α_4$, and $α_7$, with $β_2$ and/or $β_4$. Sequence information for $α_1$ is presented in *Biochem. Soc. Trans.* (1989) 17:219-220; sequence information for $α_5$ is presented in *Proc. Natl. Acad. Sci. USA* (1992) 89:1572-1576; and sequence information for $α_2$, $α_3$, $α_4$, $α_7$, $β_2$ and $β_4$ is presented elsewhere in the literature. Preferred combinations of subunits include any one or more of $α_1$, $α_2$, or $α_3$, with $β_4$; or $α_4$ or $α_7$ in combination with either $β_2$ or $β_4$. It is recognized that some of the subunits may have ion transport function in the absence of additional subunits. For example, the $α_7$ subunit is functional in the absence of any added beta subunit.

As used herein, the term "expression" refers to the process by which nucleic acid sequences are transcribed into mRNA and translated into peptides, polypeptides, or proteins. If the polynucleic acid is derived from genomic DNA, expression may, if an appropriate eukaryotic host cell or organism is selected, include splicing of the mRNA. Particularly preferred vectors for transfection of mammalian cells are the pSV2dhfr expression vectors, which contain the SV40 early promoter, mouse dhfr gene, SV40 polyadenylation and splice sites and sequences necessary for maintaining the vector in bacteria, cytomegalovirus (CMV) promoter-based vectors such as pcDNA1 (INVITROGEN, San Diego, Calif.), and MMTV promoter-based vectors such as pMSG (Catalog No. 27-4506-01 from PHARMACIA, Piscataway, N.J.).

Nicotinic AChR subunits and cells producing them may be tested by the methods provided herein or known to those of skill in the art to detect functional AChR activity. Such testing will allow the identification of pairs of alpha and beta subunit subtypes that produce functional AChRs, as well as individual subunits that produce functional AChRs. As used herein, activity of a nAChR refers to any activity characteristic of a nAChR. Such activity can typically be measured by one or more in vitro methods, and frequently corresponds to an in vivo activity of a nAChR. Such activity may be measured by any method known to those of skill in the art, such as, for example, measuring the amount of current which flows through the recombinant channel response to a stimulus. Methods to determine the presence and/or activity of nicotinic AChRs include assays that measure nicotine binding, $^{86}Rb$ ion-flux, $Ca^{2+}$ influx, the electrophysiological response of cells, the electrophysiological response of oocytes transfected with RNA from the cells, and the like.

Modulation of neuronal nicotinic AChR activity in response to contact with TMPH or a pharmaceutically acceptable salt thereof can involve comparison to a control. One type of a "control" cell or "control" culture is a cell or culture that is treated substantially the same as the cell or culture exposed to the test compound, except the control cell or culture is not exposed to the test compound (TMPH or a pharmaceutically acceptable salt thereof). For example, in methods that use voltage clamp electrophysiological procedures, the same cell can be tested in the presence and absence of TMPH or a pharmaceutically acceptable salt thereof, by merely changing the external solution bathing the cell. Another type of "control" cell or "control" culture may be a cell or a culture of cells which are identical to the transfected cells, except the cells employed for the control culture do not express functional human neuronal nicotinic AChRs. In this situation, the response of the test cell to the TMPH or pharmaceutically acceptable salt thereof is compared to the response (or lack of response) of receptor-negative (control) cell to the TMPH or pharmaceutically acceptable salt, when cells or cultures of each type of cell are exposed to substantially the same reaction conditions in the presence of compound being assayed.

In one embodiment, amphibian oocytes (e.g., *Xenopus* oocytes) are used for expression of one or more nAChR subunits, and an effective amount of TMPH, or a pharmaceutically acceptable salt thereof, is contacted with the oocytes. Methods for injecting oocytes and performing electrophysiological and other analyses for assessing receptor expression and function are described herein. While methods for in vitro transcription of cloned DNA and injection of the resulting mRNA into eukaryotic cells are well known in the art, amphibian oocytes are particularly preferred for expression of in vitro transcripts of nAChR DNA clones, including human nAChR DNA clones. See, for example, Dascal (*CRC Crit. Rev. Biochem.*, 1989, 22:317-387), for a review of the use of *Xenopus* oocytes to study ion channels.

Throughout the subject application, nicotinic acetylcholine receptor subunits are referred to by a numeral preceded by the letter of the Greek alphabet or an abbreviation. For example, the α5 subunit may also be referred to as "alpha5" or "a5".

Throughout the subject application, TMPH may be substituted with a chemical analog in connection with the compound, composition, and methods of the present invention. As used herein, the term "analogs" refers to compounds which are substantially the same as another compound but which may have been modified by, for example, adding side groups, oxidation or reduction of the parent structure. Analogs of the exemplified compounds can be readily prepared using commonly known standard reactions. These standard reactions include, but are not limited to, hydrogenation, alkylation, acetylation, and acidification reactions.

As used in this specification, including the appended claims, the singular "a", "an", and "the" include plural reference unless the contact dictates otherwise. Thus, for example, a reference to "a subunit" includes more than one such subunit. A reference to "a cell" includes more than one such cell. A reference to "a receptor" includes more than one such receptor, and so forth.

The terms "comprising", "consisting of" and "consisting essentially of" are defined according to their standard meaning. The terms may be substituted for one another throughout the instant application in order to attach the specific meaning associated with each term.

As used herein, the term "additional pharmacologically active agent" refers to any agent, such as a drug, capable of having a physiologic effect (e.g., a therapeutic or prophylactic effect) on prokaryotic or eukaryotic cells, in vivo or in vitro, including, but without limitation, chemotherapeutics, toxins, radiotherapeutics, radiosensitizing agents, gene therapy vectors, antisense nucleic acid constructs or small interfering RNA, imaging agents, diagnostic agents, agents known to interact with an intracellular protein, polypeptides, and polynucleotides.

The additional pharmacologically active agent can be selected from a variety of known classes of drugs, including, for example, analgesics, anesthetics, anti-inflammatory agents, anthelmintics, anti-arrhythmic agents, antiasthma agents, antibiotics (including penicillins), anticancer agents (including Taxol), anticoagulants, antidepressants, antidiabetic agents, antiepileptics, antihistamines, antitussives, antihypertensive agents, antimuscarinic agents, antimycobacterial agents, antineoplastic agents, antioxidant agents, antipyretics, immunosuppressants, immunostimulants, antithyroid agents, antiviral agents, anxiolytic sedatives (hypnotics and neuroleptics), astringents, bacteriostatic agents, beta-adrenoceptor blocking agents, blood products and substitutes, bronchodilators, buffering agents, cardiac inotropic agents, chemotherapeutics, contrast media, corticosteroids, cough suppressants (expectorants and mucolytics), diagnostic agents, diagnostic imaging agents, diuretics, dopaminergics (antiparkinsonian agents), free radical scavenging agents, growth factors, haemostatics, immunological agents, lipid regulating agents, muscle relaxants, proteins, peptides and polypeptides, parasympathomimetics, parathyroid calcitonin and biphosphonates, prostaglandins, radiopharmaceuticals, hormones, sex hormones (including steroids), time release binders, anti-allergic agents, stimulants and anoretics, steroids, sympathomimetics, thyroid agents, vaccines, vasodilators, and xanthines.

The additional pharmacologically active agent need not be a therapeutic agent. For example, the agent may be cytotoxic to the local cells to which it is delivered but have an overall beneficial effect on the subject. Further, the agent may be a diagnostic agent with no direct therapeutic activity per se, such as a contrast agent for bioimaging.

MATERIALS AND METHODS

Synthesis. Chemicals used for the synthesis were purchased from ALDRICH Chemical Company. Compounds were characterized by $^1$H-NMR and FAB-MS.

TMPH Synthesis. To a mixture of 2,2,6,6-tetramethyl-4-piperidinol (472 mg, 3.0 mmol) and methyl heptanoate (476 mg, 3.3 mmol) in 3.0 mL of dimethyl formamide was added 250 mg of powdered potassium carbonate. The resulting mixture was heated at 145~155° C. for 64 hours under a gentle stream of $N_2$. After cooling, the reaction mixture was partitioned between water and hexanes. The organic layer was separated, washed with water (2×) and brine, then dried over anhydrous $MgSO_4$ and evaporated to afford the crude product as an oil. The oil was dissolved in MeOH and was then treated with 2 equivalents of conc. HCl. The solvent was removed in vacuo, and the residue was then treated with diethyl ether. The resulting solids were removed by filtration. The ethereal filtrate was concentrated in vacuo and triturated with hexane to afford 380 mg (41%) of TMPH hydrochloride. It was recrystallized from boiling ethyl acetate/hexane to afford short colorless needles, mp 113-115° C. FAB-HRMS: calculated ($C_{16}H_{32}NO_2$): 270.2433 found: 270.2435.

In vivo Studies

Animals. Male ICR mice (20-25 g) obtained from Harlan Laboratories (Indianapolis, Ind.) were used throughout the study. Animals were housed in groups of six and had free access to food and water. Adult, male Long-Evans rats (350-460 g), obtained from Harlan (Dublin, Va.), were individually housed in a temperature-controlled (20-22° C.) environment with a 12-hour light-dark cycle (lights on at 7 a.m.). Rats were maintained within the indicated weight range by restricted post-session feeding and had ad libitum water in their home cages. Rats were drug-naive at the beginning of the study. Animals were housed in an AALAC approved facility and the study was approved by the Institutional Animal Care and Use Committee of Virginia Commonwealth University.

Drugs. Mecamylamine hydrochloride was supplied as a gift from Merck, Sharp and Dohme & Co. (West Point, Pa.). (−)-Nicotine was obtained from Aldrich Chemical Company, Inc. (Milwaukee, Wis.) and converted to the ditartrate salt as described by Aceto et al. (Aceto et al. *J Med Chem,* 1979, 22:174-177. All drugs were dissolved in physiological saline (0.9% sodium chloride). All doses are expressed as the free base of the drug.

Behavioral Assays

Locomotor Activity. Mice were placed into individual Omnitech photocell activity cages (28×16.5 cm) immediately after s.c. administration of either 0.9% saline or nicotine (6.2 mmol/kg or 1 mg/kg) and were allowed to acclimate for 10 minutes. Interruptions of the photocell beams (two banks of eight cells each) were then recorded for the next 10 minutes. Data were expressed as percentage of depression where % depression=[1−(counts from nicotine-treated animals/counts from vehicle-treated animals)]×100. Mice were pretreated s.c. with either saline or TMPH 10 minutes before nicotine.

Antinociception.

1. Tail-flick test. Antinociception was assessed by the tail-flick method of D'Amour and Smith (D'Amour and Smith *J. P. E. T.,* 1941, 72:74-79) as modified by Dewey et al. (Dewey et al. *J Pharmacol Exp Ther,* 1970, 175:435-442). Briefly, mice were lightly restrained while a radiant heat source was shone onto the upper portion of the tail. Latency to remove the tail from the heat source was recorded for each animal. A control response (2-4 seconds) was determined for each mouse before treatment, and a test latency was determined after drug administration. In order to minimize tissue damage, a maximum latency of 10 seconds was imposed. Antinociceptive response was calculated as percent maximum possible effect (% MPE), where % MPE=[(test−control)/(10−control)]×100.

2. Hot-plate Test. Mice were placed into a 10 cm wide glass cylinder on a hot plate (Thermojust Apparatus) maintained at 55.0° C. Two control latencies at least 10 minutes apart were determined for each mouse. The normal latency (reaction time) was 8 to 12 seconds. Antinociceptive response was calculated as percent maximum possible effect (% MPE), where % MPE=[(test−control)/(40−control)×100]. The reaction time was scored when the animal jumped or licked its paws. In order to minimize tissue damage, a maximum latency of 40 seconds was imposed. Antagonism studies were carried out by pretreating the mice with either saline or TMPH 10 minutes before nicotine. The animals were tested 5 minutes after administration of nicotine.

Body Temperature. Rectal temperature was determined by a thermistor probe (inserted 24 mm) and digital thermometer (Yellow Springs Instrument Co., Yellow Springs, Ohio). Readings were taken just before and 30 minutes after the s.c. injection of nicotine at a dose of 12.3 μmol/kg (2 mg/kg). Mice were pretreated with either saline or TMPH (s.c.) 10 minutes before nicotine. The difference in rectal temperature before and after treatment was calculated for each mouse. The ambient temperature of the laboratory varied from 21-24° C. from day to day.

The doses of nicotine used in the different tests represent approximately an $ED_{84}$ (Effective dose 84%) which were determined from previous works (Damaj et al. *Psychopharmacology (Berl),* 1995, 117:67-73). Eight to twelve mice were tested in each treatment group and each animal was tested only once.

Drug Discrimination in Rats.

1. Apparatus: Rats were trained and tested in standard operant conditioning chambers (Lafayette Instruments Co., Lafayette, Ind.) housed in sound-attenuated cubicles. Each chamber had three retractable levers, only two of which were used for this study. Pellet dispensers delivered 45-mg BIO SERV (Frenchtown, N.J.) food pellets to a food cup on the front wall of the chamber between the two response levers and over the third (retracted) lever. Fan motors provided ventilation and masking noise for each chamber. House lights located above the food cup were illuminated during training and testing sessions. A micro-computer with Logic '1' interface (MED Associates, Georgia, Vermont) and MED-PC software (MED Associates) was used to control schedule contingencies and to record data.

2. Procedure: Rats were trained to press one lever following administration of 0.4 mg/kg nicotine and to press another lever after injection with saline, each according to a fixed-ratio 10 schedule of food reinforcement. Completion of 10 consecutive responses on the injection-appropriate lever resulted in delivery of a food reinforcer. Each response on the incorrect lever reset the ratio requirement on the correct lever. The position of the drug lever was varied among the group of rats. The daily injections for each rat were administered in a double alternation sequence of 0.4 mg/kg nicotine and saline. Rats were injected and returned to their home cages until the start of the experimental session 5 minutes later. Training occurred during sessions conducted five days a week (Monday-Friday) until the rats had met three criteria during eight of ten consecutive sessions: (1) first completed fixed ratio 10 on the correct lever, (2) percentage of correct-lever responding >80% for the entire session, and (3) response rate >0.4 responses/sec.

Following successful acquisition of the discrimination, stimulus substitution tests with test compounds were conducted on Tuesdays and Fridays during 15-minute test sessions. Training continued on Mondays, Wednesdays, and Thursdays. During test sessions, responses on either lever delivered reinforcement according to a fixed ratio 10 schedule. In order to be tested, rats must have completed the first FR and made at least 80% of all responses on the injection-appropriate lever on the preceding day's training session. In addition, the rat must have met these same criteria during at least one of the training sessions with the alternate training compound (nicotine or saline) earlier in the week.

A nicotine dose-effect determination [0.1, 0.2, 0.4, 0.8, and 1.2 mg/kg] was performed first in each rat. Then, combination tests with nicotine, and TMPH followed (see figures for specific doses). Doses of each compound were administered in ascending order. Throughout the study, control tests with saline and 0.4 mg/kg nicotine were conducted during the week before the start of each dose-effect curve determination.

Statistical Analysis. Statistical analysis of all analgesic and in vivo studies was performed using either t-test or analysis of variance (ANOVA) with Tukey's test post hoc test when appropriate. All differences were considered significant at p<0.05. $AD_{50}$ values with 95% CL for behavioral data were calculated by unweighted least-squares linear regression as described by Tallarida and Murray (Tallarida and Murray *Manual of Pharmacological Calculations with Computer Programs*. 1987, Springer-Verlag, N.Y.).

Expression in *Xenopus* Oocytes

Animals: *Xenopus*

Mature (>9 cm) female *Xenopus laevis* African frogs (NASCO, Ft. Atkinson, Wis.) were used as a source of oocytes. Prior to surgery, frogs were anesthetized by placing the animal in a 1.5 g/l solution of MS222 (3-aminobenzoic acid ethyl ester) for 30 minutes. Oocytes were removed from an incision made in the abdomen.

In order to remove the follicular cell layer, harvested oocytes were treated with 1.25 mg/ml collagenase from Worthington Biochemical Corporation (Freehold, N.J.) for 2 hours at room temperature in calcium-free Barth's solution (88 mM NaCl, 10 mM HEPES pH 7.6, 0.33 mM $MgSO_4$, 0.1 mg/ml gentamicin sulfate). Subsequently, stage 5 oocytes were isolated and injected with 50 nl (5-20 ng) each of the appropriate subunit cRNAs. Recordings were made 2 to 15 days after injection.

Preparation of RNA

Rat neuronal nAChR clones and mouse muscle nAChR cDNA clones were used. The wild-type clones were obtained from Dr. Jim Boulter (UCLA). The rat α6/3 (Dowell et al. *J Neurosci*, 2003, 23:8445-8452) clone was obtained from Michael McIntosh (University of Utah) and expressed in *Xenopus* oocytes in combinations with rat β2 and β3. The original α6/3 construct provided was sequenced and was found to have a mutation in the second transmembrane domain (TM2) sequence which exchanged a valine for an alanine in the 7' position (TM2 numbering scheme (Miller, *Neuron*, 1989, 2:1195-1205)). The TM2 domain is understood to line the pore of the channel, with alpha helix structure. The 7' position may actually be directed away from the actual pore lining, but this residue is highly conserved in all of the nAChR. It is valine in all of them except α9 (isoleucine) and β1, where it is alanine. The TM2 mutation in the α6/3 chimera was corrected by using QuickChange (Stratagene) according to their protocols. The corrected α6/3 chimera sequence was confirmed by restriction diagnostics and by automated fluorescent sequencing (University of Florida core facility). The corrected clone was expressed as above in *Xenopus* oocytes with β2 and β3 and compared to the wild-type α3 co-expressed with β2 and β3.

After linearization and purification of cloned cDNAs, RNA transcripts were prepared in vitro using the appropriate mMessage mMachine kit from Ambion Inc. (Austin, Tex.).

Electrophysiology. The majority of experiments were conducted using OpusXpress 6000A (Axon Instruments, Union City Calif.). OpusXpress is an integrated system that provides automated impalement and voltage clamp of up to eight oocytes in parallel. Cells were automatically perfused with bath solution, and agonist solutions were delivered from a 96-well plate. Both the voltage and current electrodes were filled with 3 M KCl. The agonist solutions were applied via disposable tips, which eliminated any possibility of cross-contamination. Drug applications alternated between ACh controls and experimental applications. Flow rates were set at 2 ml/min for experiments with α7 receptors and 4 ml/min for other subtypes. Cells were voltage-clamped at a holding potential of −60 mV. Data were collected at 50 Hz and filtered at 20 Hz. Agonist applications were 12 seconds in duration followed by 181-second washout periods for α7 receptors and 8 seconds with 241-second wash periods for other subtypes. For some experiments, particularly under conditions where residual inhibition precluded making repeated measurements from single cells (see below), manual oocyte recordings were made as previously described (Papke and Papke *Br J of Pharmacol*, 2002, 137:49-61). In brief, Warner Instruments (Hamden, Conn.) OC-725C oocyte amplifiers were used, and data were acquired with a minidigi or digidata 1200A with pClamp9 software (Axon Instruments). Sampling rates were between 10 and 20 Hz and the data were filtered at 6 Hz. Cells were voltage clamped at a holding potential of −50 mV. Data obtained with these methods were comparable to those obtained with OpusXpress.

Experimental Protocols and Data Analysis. Each oocyte received two initial control applications of ACh, an experimental drug application (or co-application of ACh and TMPH), and then follow-up control application(s) of ACh. The control ACh concentrations for α1β1γδ, α3β4, α4β2, α3β2, α3β2α5, α3β2β3, α6/3β2β3 α6β4β3 and α7, receptors were 30 μM, 100 μM, 10 μM, 30 μM, 1 μM 100 μM 100 μM 100 μM and 300 μM, respectively. In other experiments (Papke et al. *J. Neurochem.*, 2000, 75:204-216; Papke and Papke *Br J of Pharmacol*, 2002, 137:49-61) these concentrations were determined to be the $EC_{74}$, $EC_{15}$, $EC_{22}$, $EC_{17}$, $EC_{40}$, $EC_{70}$, $EC_{55}$, $EC_{70}$ and $EC_{100}$, respectively. These concentrations were selected since they gave large responses with relatively little desensitization so that the same oocyte could be stimulated repeatedly with little decline in the amplitude of the ACh responses. This allowed the inhibitory effects of the antagonist to be separated out from possible cumulative desensitization.

Responses to experimental drug applications were calculated relative to the preceding ACh control responses in order to normalize the data, compensating for the varying levels of channel expression among the oocytes. Responses were characterized based on both their peak amplitudes and the net charge (Papke and Papke *Br J of Pharmacol*, 2002, 137:49-61). In brief, for net charge measurement a 90-second segment of data beginning 2 seconds prior to drug application was analyzed from each response. Data were first adjusted to account for any baseline offset by subtracting the average value of 5-second period of baseline prior to drug application from all succeeding data points. When necessary, baseline reference was also corrected for drift using Clampfit 9.0 (AXON Instruments, Union City Calif.). Following baseline correction, net charge was then calculated by taking the sum of all the adjusted points. The normalized net charge values were calculated by dividing the net charge value of the experimental response by the net charge value calculated for the preceding ACh control response. Means and standard errors (SEM) were calculated from the normalized responses of at least 4 oocytes for each experimental concentration. In order to measure the residual inhibitory effects, this subsequent control response was compared to the pre-application control ACh response.

For concentration-response relations, data derived from net charge analyses were plotted using Kaleidagraph 3.0.2 (Abelbeck Software; Reading, Pa.), and curves were generated from the Hill equation $$\text{Response} = \frac{I_{max}[agonist]^n}{[agonist]^n + (EC50)^n}$$

where $I_{max}$ denotes the maximal response for a particular agonist/subunit combination, and n represents the Hill coefficient. $I_{max}$, n, and the $EC_{50}$ were all unconstrained for the fitting procedures. Negative Hill slopes were applied for the calculation of $IC_{50}$ values.

Example 1—Effects of TMPH on Nicotine's Actions in vivo

Antinociception

Figure 1B:
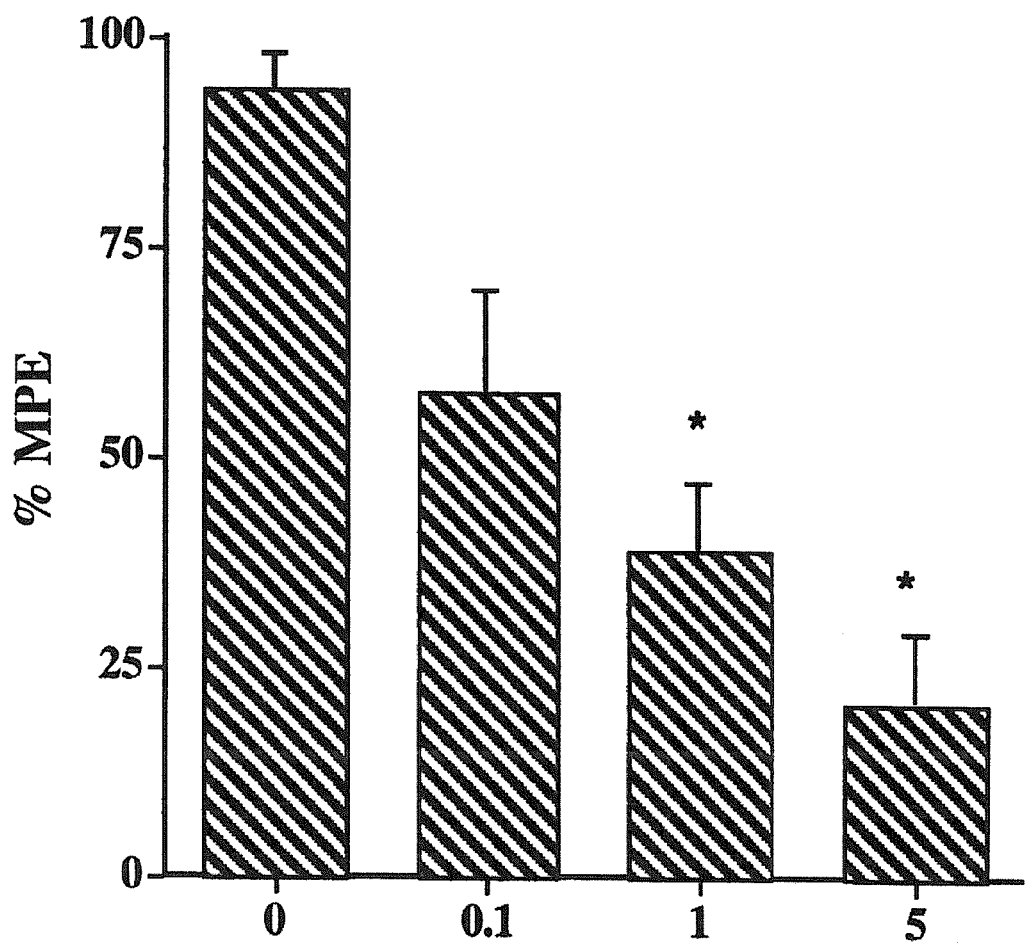

Nicotine-induced antinociception in the tail-flick and hot-plate tests after systemic administration in mice (2.5 mg/kg) was blocked by TMPH in a dose-dependent manner (FIGS. 1A-1B). Calculation of the $AD_{50}$ showed that TMPH is 1.7 times more potent in blocking the antinociceptive effect of nicotine in the hot-plate than in tail-flick test (0.7 versus 1.2 mg/kg). By itself, TMPH after s.c. injection did not cause antinociception at the indicated doses and times.

Time-course of TMPH Effects

Figure 2:
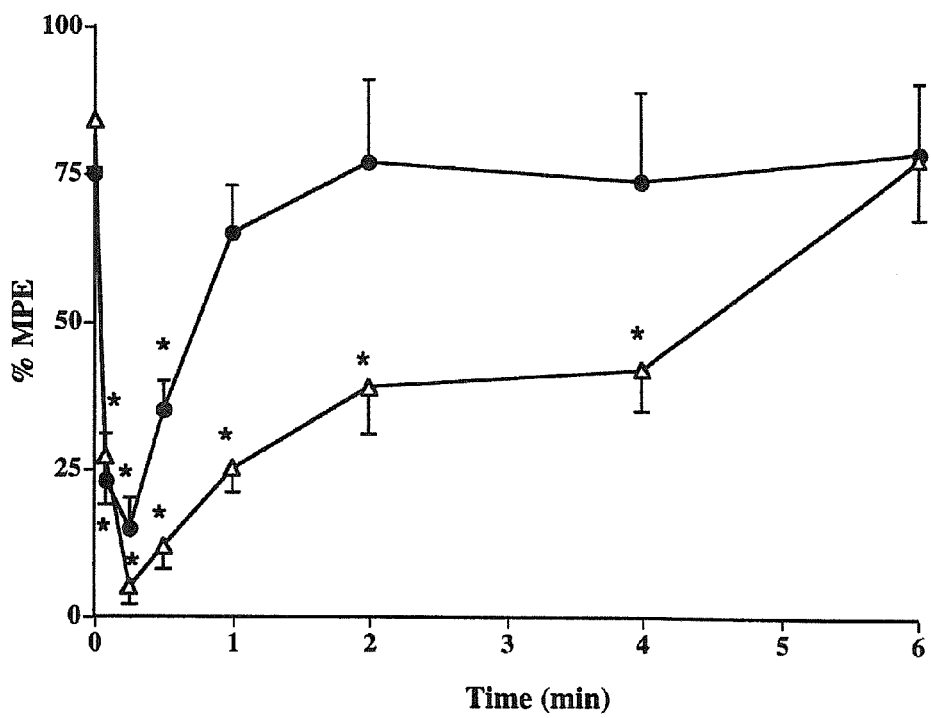
FIG. 2 shows the time-course of TMPH effect on nicotine-induced antinociception (2.5 mg/kg) in (—△—) the tail-flick and (—●—) the hot-plate tests after s.c. administration of 5 mg/kg in mice. Each point represents the mean±SE of 8 to 12 mice. *p<0.05 compared to correspondent zero time point.

The duration of action of TMPH in the tail-flick test was time-dependent with maximum blockade occurring between 15 and 30 minutes after a dose of 5 mg/kg dose. The effect of TMPH lasted for at least 4 hours after its administration. Indeed, as illustrated in FIG. 2, nicotine's effect started to recover within 60 minutes after pretreatment with a dose of 5 mg/kg of TMPH, but was still significantly different from control 4 hours after. Similar to the tail-flick test, TMPH time-dependently blocked nicotine-induced antinociception as measured by the hot-plate test, however with a shorter duration of action. As shown in FIG. 2, 60 minutes after pretreatment with a dose of 5 mg/kg of TMPH the effect of nicotine recovered fully to the pre-treatment value.

Locomotor Activity and Body Temperature

TMPH at 20 mg/kg administered s.c. 15 minutes prior to the injection of nicotine (1.5 mg/kg) failed to significantly reduce the hypomotility induced by nicotine (Table 1). In addition, nicotine-induced hypothermia after systemic administration in mice (2.5 mg/kg) was also not blocked by TMPH given at 20 mg/kg. By itself, TMPH after s.c. injection did not have a significant effect on the body temperature or the locomotor activity at the indicated doses and times.

TABLE 1

Effect of TMPH on nicotine-induced hypomotility and hypothermia after s.c. administration. Each point represents the mean ± SE of 6 to 8 mice.

| Treatment (mg/kg) | Locomotor Activity # Interrupts (Mean ± SEM) | Body temperature Δ° C. (Mean ± SEM) |
|---|---|---|
| Saline/Saline | 1931 ± 120 | −0.3 ± 0.1 |
| TMPH (20)/Saline | 2031 ± 160 | −1.0 ± 0.2 |
| Saline/Nicotine (1.5) | 358 ± 92* | −5.0 ± 0.3* |
| TMPH (20)/Nicotine (1.5) | 397 ± 170* | −5.2 ± 0.4* |

*P < 0.05 from Saline/Saline

Nicotine Discriminative Stimulus in Rats

Figure 3A:
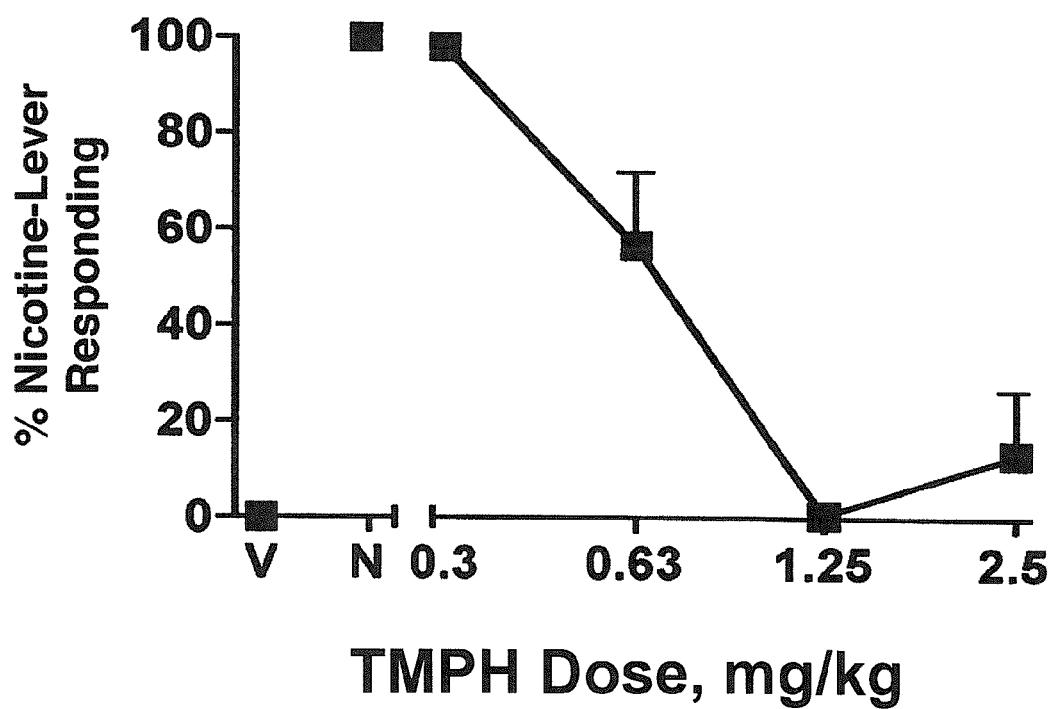
FIGS. 3A-3B show the effects of PC-7 in combination with 0.4 mg/kg nicotine on percentage of nicotine-lever responding (FIG. 3A) and response rates (FIG. 3B) in rats trained to discriminate 0.4 mg/kg nicotine from vehicle. Points above V and N represent the results of control tests with two saline injections and saline plus 0.4 mg/kg nicotine, respectively, conducted before the dose-effect curve determination. Each value represents the mean (±SEM) of 4-6 rats.
Figure 3B:
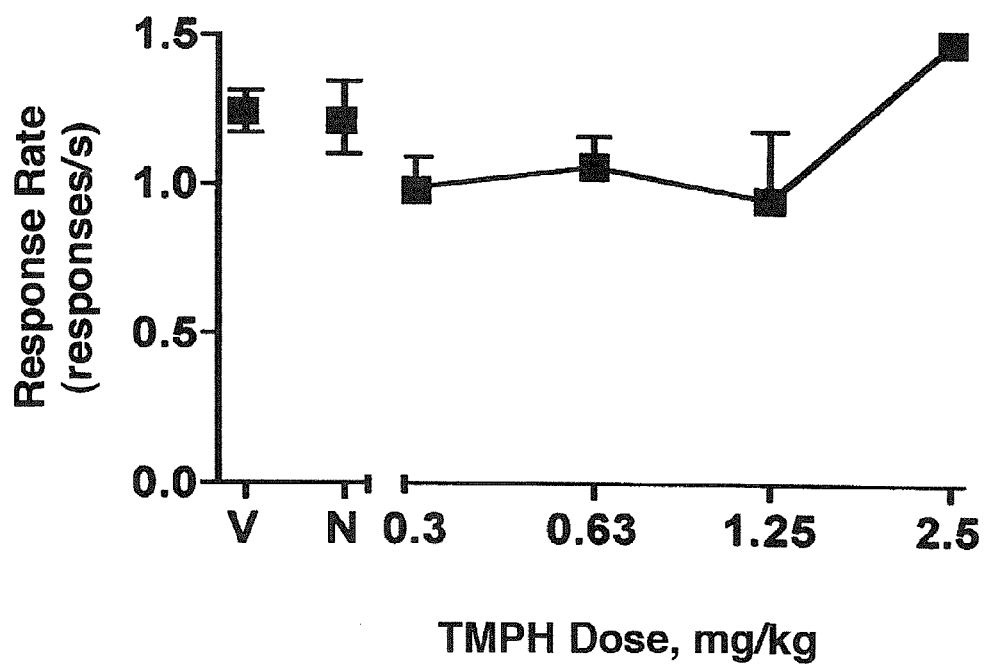

FIGS. 3A-3B shows the results of combination tests with the training dose of nicotine and various doses of TMPH. TMPH dose-dependently antagonized the discriminative stimulus effects of 0.4 mg/kg nicotine (FIG. 3A) with an $AD_{50}$ value of 0.74 mg/kg (0.56-0.98) (Table 2). The TMPH-nicotine combination did not alter response rates (compared to vehicle) at any of the dose combinations tested (p>0.05; FIG. 3B). TMPH alone also did not produce nicotine-lever responding at the doses at which antagonism was observed (data not shown).

TABLE 2

Comparison of the blockade potency of TMPH and mecamylamine on nicotine's pharmacological and behavior effects after systemic and administration in mice and rats.

| Test | TMPH[a] ($AD_{50}$ mg/kg ± CL) | Mecamylamine[b] ($AD_{50}$ mg/kg ± CL) |
|---|---|---|
| Tail-flick | 1.2 (0.6-1.8) | 0.045 (0.03-0.1) |
| Hot-plate | 0.7 (0.3-1.7) | 0.8 (0.5-1.1) |
| Drug discrimination | 0.74 (0.56-0.98) | 0.91 (0.63-1.32) |
| Hypothermia | 0% blockade @20 | 1.2 (0.9-1.8) |
| Hypomotility | 0% blockade @20 | 1.95 (1.1-2.5) |

[a]$AD_{50}$ values (±CL) were calculated from the dose-response and expressed as mg/kg. Each dose group included 6 to 8 animals.
[b]$AD_{50}$ values (±CL) were taken from Damaj et al. (*Psychopharmacology (Berl)*, 1995, 117: 67-73) and Wiley et al. (*Exp Clin Psychopharmacol*, 2002, 10: 129-135).

Example 2—Effects of TMPH on nAChR Expressed in *Xenopus* Ooces

TMPH Inhibition of AChR Subtypes

Figure 4A:
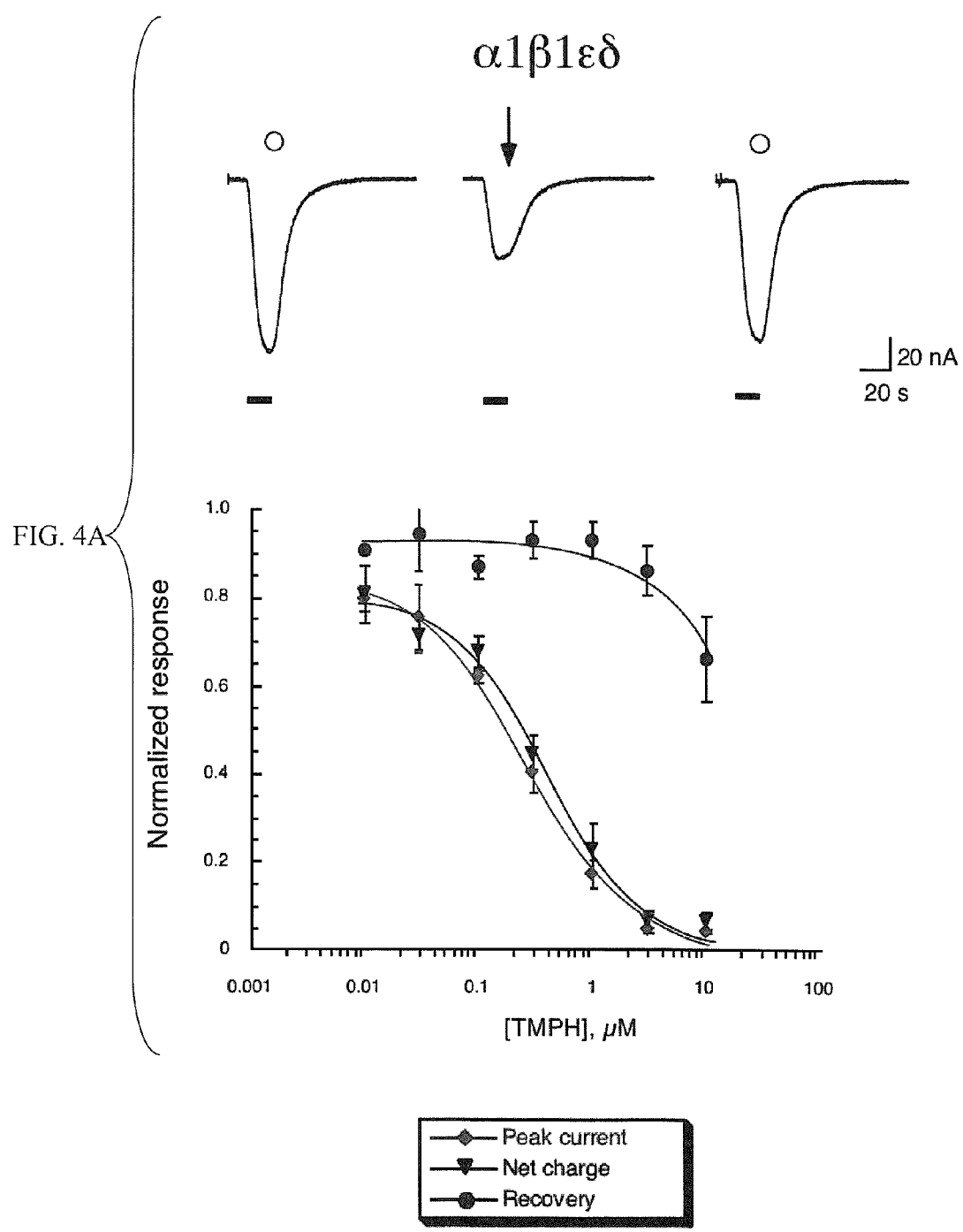
FIGS. 4A-4B show that TMPH produces selective long-term inhibition of neuronal ganglionic type $\alpha 3 \beta 4$ receptors.
Figure 4B:
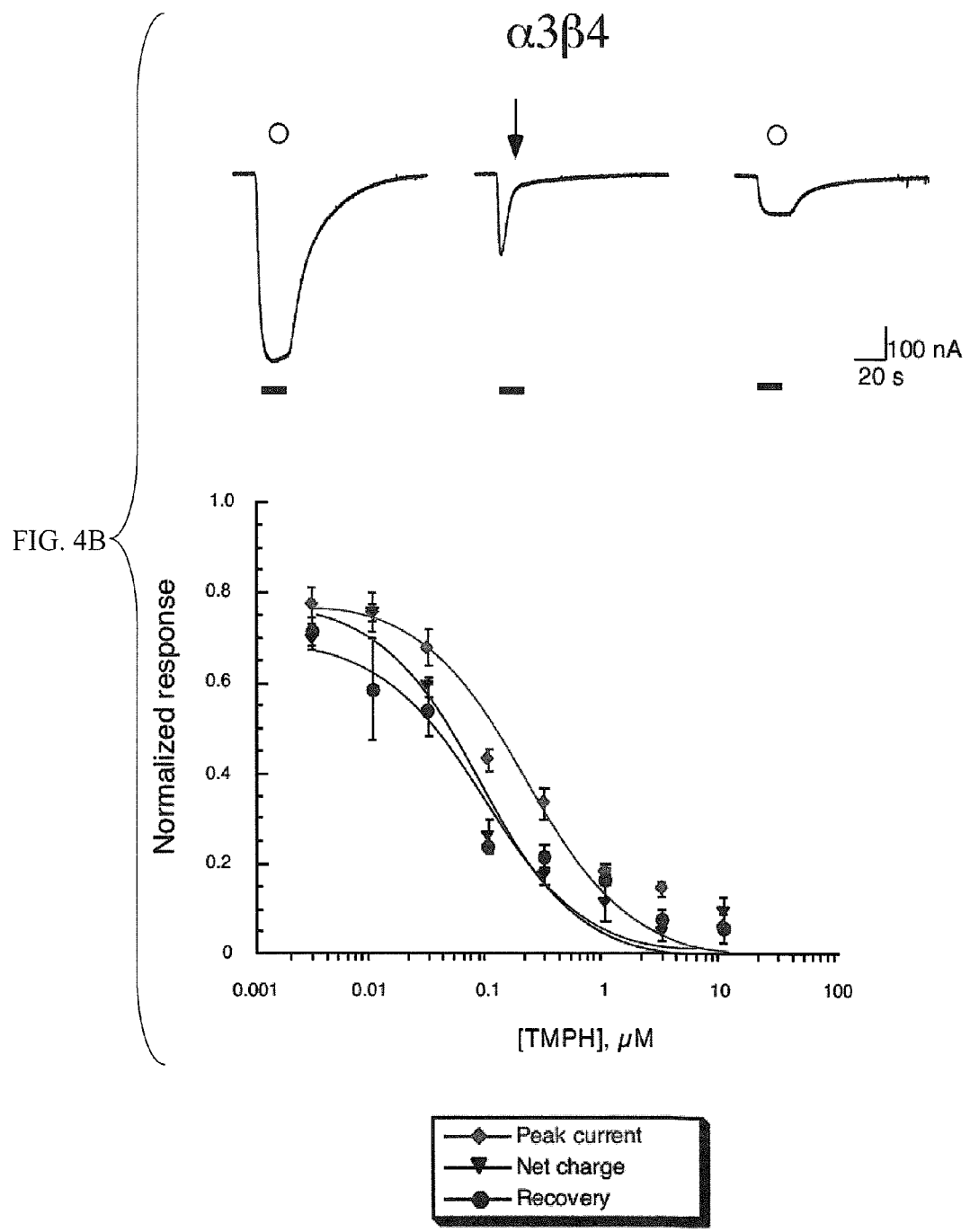
Figure 5A:
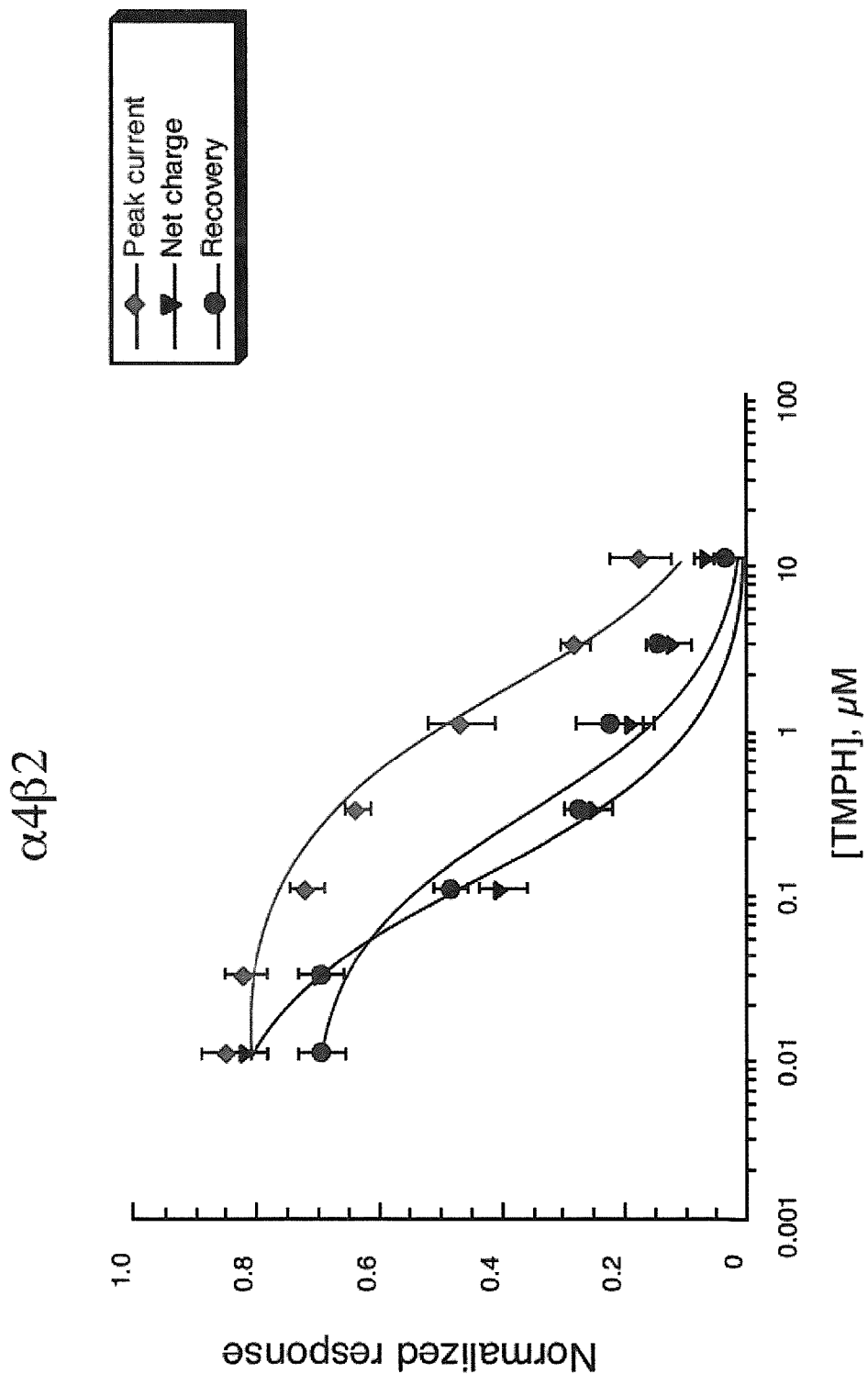
FIGS. 5A-5C show that TMPH produces long-term inhibition of neuronal beta subunit-containing nAChR but not α7 homomeric receptors. Shown are the averaged normalized data (±SEM, n≥4) from oocytes expressing α4β2, α3β2, and α7 subunits (FIGS. 5A-5C, respectively) to the co-application ACh and a range of TMPH concentrations. Three values are plotted in each of the concentration-response curves: (♦) the peak current amplitude of the co-application response, normalized to the peak amplitude of the previous ACh control; (▼) the net charge of the co-application response, normalized to the net charge of the previous ACh control; and (●) the peak current amplitude of the ACh control response obtained after the TMPH/ACh co-application, normalized to the peak amplitude of the previous ACh control. The control ACh concentrations used were 10 μM, 30 μM, and 300 μM for α4β2, α3β2, and α7, respectively.
Figure 5B:
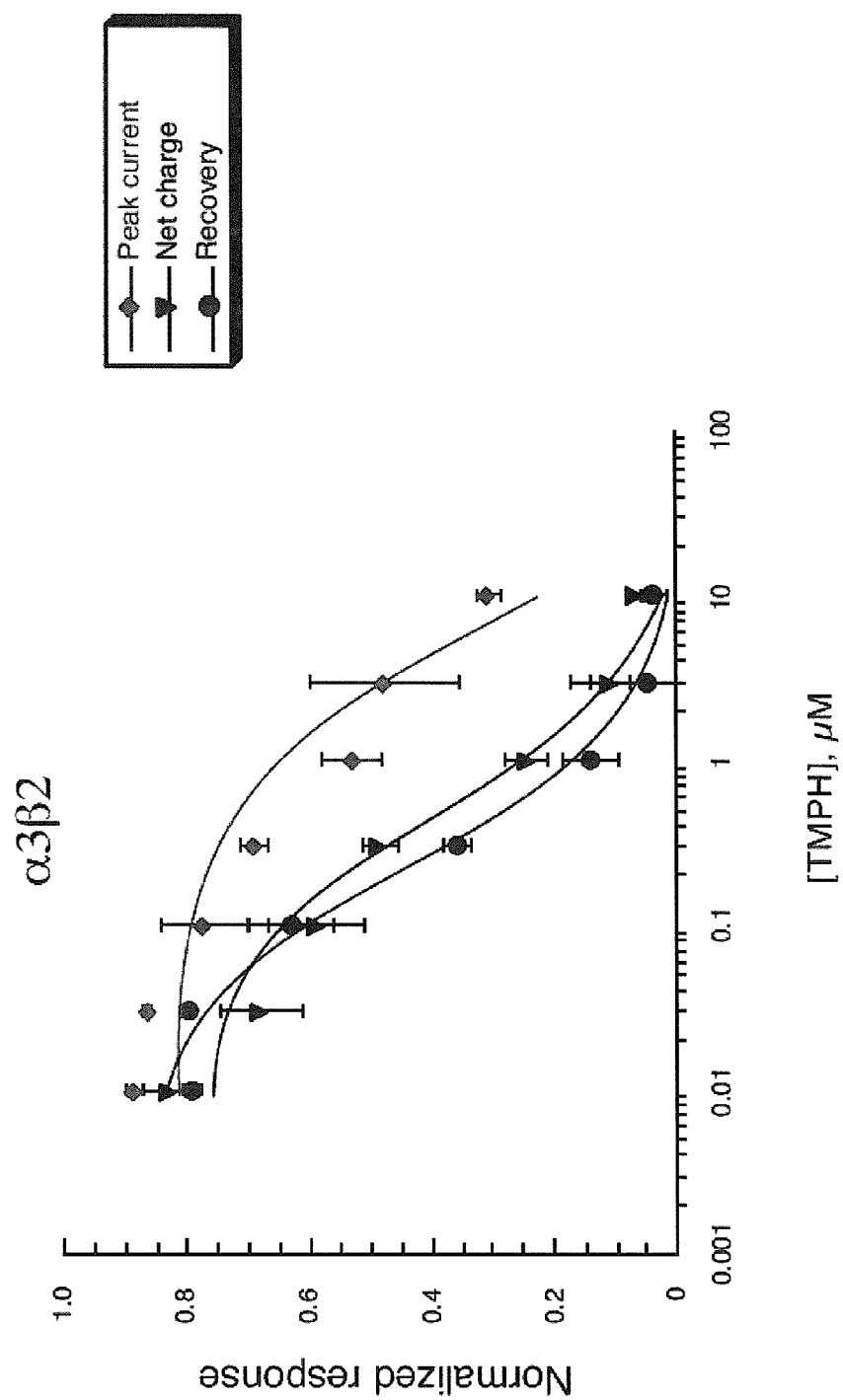
Figure 5C:
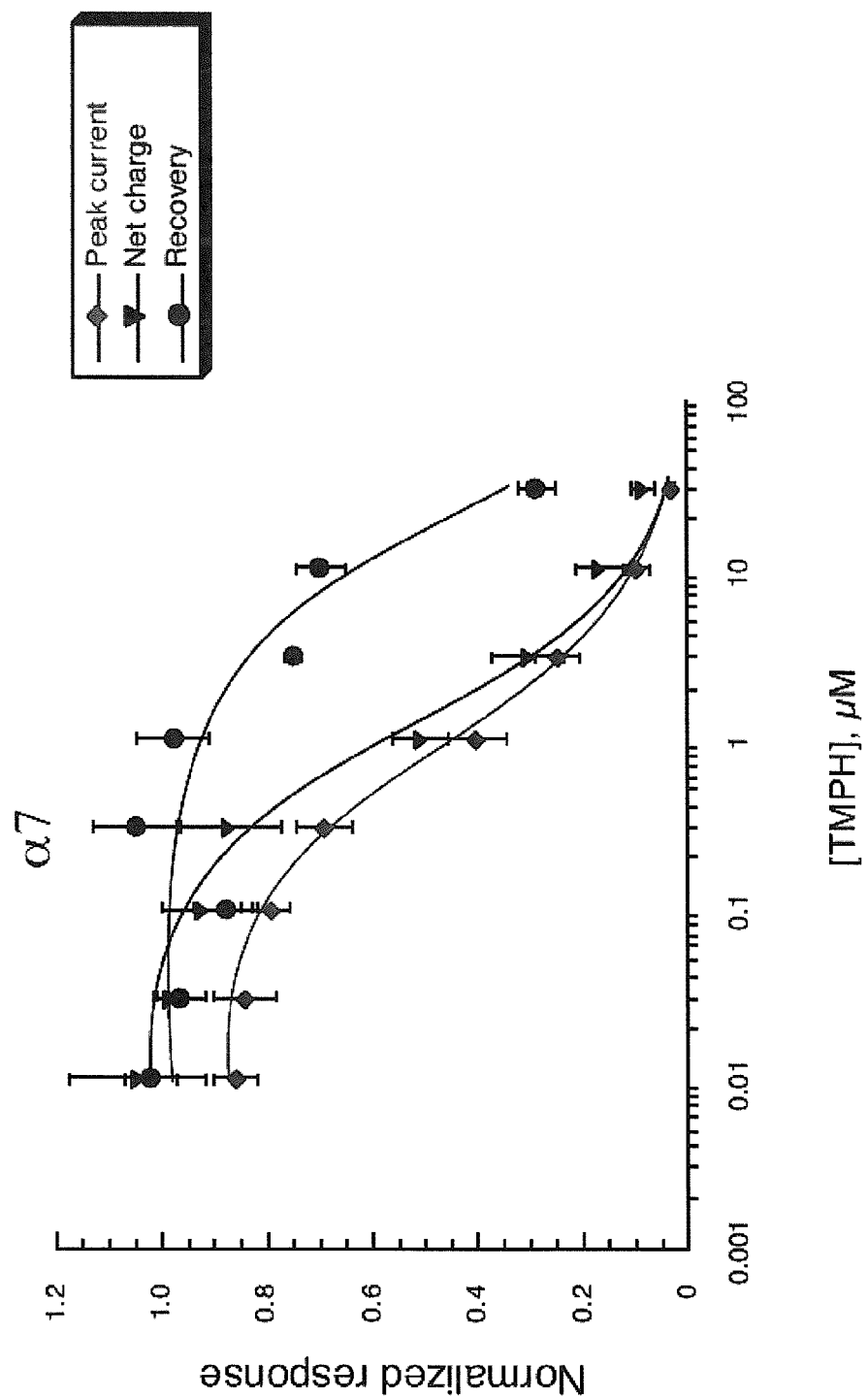

TMPH was initially tested on mouse muscle-type ($\alpha1\beta1\epsilon\delta$) nAChR, three different pairwise combinations of rat neuronal alpha and beta subunits ($\alpha3\beta4$, $\alpha4\beta2$, and $\alpha3\beta2$), and $\alpha7$ homomeric neuronal nAChR. Additionally combinations of three subunits and an $\alpha6/3$ chimera were tested. The results are summarized in Table 3. As shown in FIGS. 4A-4B, both muscle-type and ganglionic-type ($\alpha3\beta4$) receptors were inhibited during the co-application of ACh and TMPH. However, while the inhibition of muscle-type receptors was readily reversible after a 5-minute wash, the inhibition of $\alpha3\beta4$ receptors persisted after the wash. The data also indicate that the inhibition of $\alpha3\beta4$ receptors became progressively greater during the co-application response so that the inhibition of net charge was greater than the inhibition of peak current. This was not the case for the inhibition of muscle-type receptors. The other neuronal alpha-beta subunit pairs tested, $\alpha4\beta2$ and $\alpha3\beta2$, were blocked in a fashion similar to $\alpha3\beta4$ receptors (FIGS. 5A-5C), with a larger inhibition of net charge than peak current and virtually no recovery following a 5-minute wash. In contrast, $\alpha7$ receptors, like muscle-type receptors, showed little difference between the inhibition of peak currents and net charge and showed significant recovery after a 5-minute wash (FIGS. 5A-5C). These differences are reflected in the $IC_{50}$ values presented in Table 3. Note that receptors that rapidly equilibrate inhibition and recover readily (e.g. muscle-type receptors and $\alpha7$) have ratios of the $IC_{50}$ for net charge to the $IC_{50}$ for peak currents of close to 1 (Table 4), while for the receptors which show progressively more inhibition during the co-application and have slow recovery, the ratio of the $IC_{50}$ for net charge to the $IC_{50}$ for peak currents is much less than 1 and $IC_{50}$ values estimated from the inhibition of net charge are similar to those which can be derived from persistent inhibition measured after a 5-minute wash (i.e. from the recovery data, see Table 4).

TABLE 3

| | In vitro data. | | |
|---|---|---|---|
| | $IC_{50}$(peak) | $IC_{50}$(area) | $IC_{50}$(recovery) |
| Mouse Muscle | 276 ± 20 nM | 390 ± 50 nM | 27 ± 5.5 μM |
| Rat α7 | 1.0 ± 0.1 μM | 1.2 ± 0.2 μM | 16 ± 4 μM |
| Rat α4β2 | 1.4 ± 0.3 μM | 110 ± 40 nM | 250 ± 80 nM |
| Rat α3β4 | 200 ± 50 nM | 75 ± 23 nM | 85 ± 32 nM |
| Rat α3β2 | 3.7 ± 1.2 μM | 440 ± 90 nM | 230 ± 30 nM |
| Human α3β2 | 3.7 ± 1.2 μM | 460 ± 170 nM | 400 ± 120 nM |
| Human α3β2α5 | 1.1 ± μM | 430 ± 180 nM | 750 ± 200 nM |
| Rat α3β2β3 | 120 ± 80 μM | 2.7 ± 0.6 μM | 4.3 ± 1.5 μM |
| Rat α6/3β2β3 | 60 ± 20 μM | 1.0 ± 0.3 μM | 2.3 ± 0.5 μM |

TABLE 3-continued

In vitro data.

| | $IC_{50}$(peak) | $IC_{50}$(area) | $IC_{50}$(recovery) |
|---|---|---|---|
| Rat α3β4β3 | 1.9 ± 0.2 μM | 1.4 ± 0.2 μM | 30 ± 50 μM, 1.0 ± 0.6 μM* |
| Rat α6β4β3 | 11.0 ± 4.4 μM | 18.3 ± 4.9 μM | 1700 ± 420 μM |

IC50 values were calculated based on either the decrease in peak current amplitudes or the decrease in the net charge of the ACh response when co-applied with TMPH. For many of the subunit combinations tested there was no detectable recovery after a 5-minute wash and so $IC_{50}$ values were also calculated based on the inhibition still present at the 5-minute time point (recovery).
*The data for the recovery of cells expressing a3b4b3 was fit to a 2 site model (see FIGS. 12A-12B).

TABLE 4

In vitro data.

| | $IC_{50}$net charge/$IC_{50}$peak | $IC_{50}$recovery/$IC_{50}$net charge |
|---|---|---|
| mouse α1β1δε | 1.4 | 69 |
| rat α7 | 1.2 | 13.3 |
| rat α4β2 | 0.08 | 2.3 |
| rat α3β4 | 0.36 | 1.1 |
| rat α3β2 | 0.12 | 0.52 |
| human α3β2 | 0.12 | 0.87 |
| human α3β2α5 | 0.15 | 1.7 |
| rat α3β2β3 | 0.025 | 1.6 |
| rat α6/3β2β3 | .017 | 2.0 |
| rat α3β4β3 | 0.74 | 0.7, 21* |
| rat α6β4β3 | 1.7 | 93 |

The value "$IC_{50}$ (recovery)" reflects the residual inhibition of the ACh control response measured after a 5-minute wash. If $IC_{50}$(recovery) > $IC_{50}$(area), then there was significant recovery (i.e. readily reversible inhibition). Likewise if $IC_{50}$(area) < $IC_{50}$(peak), then there was significant buildup of inhibition throughout the agonist/antagonist co-application.
*The data for the recovery of cells expressing a3b4b3 was fit to a 2-site model (see FIGS. 12A-12B).

Neuronal nAChR Recovery Rates

Figure 6:
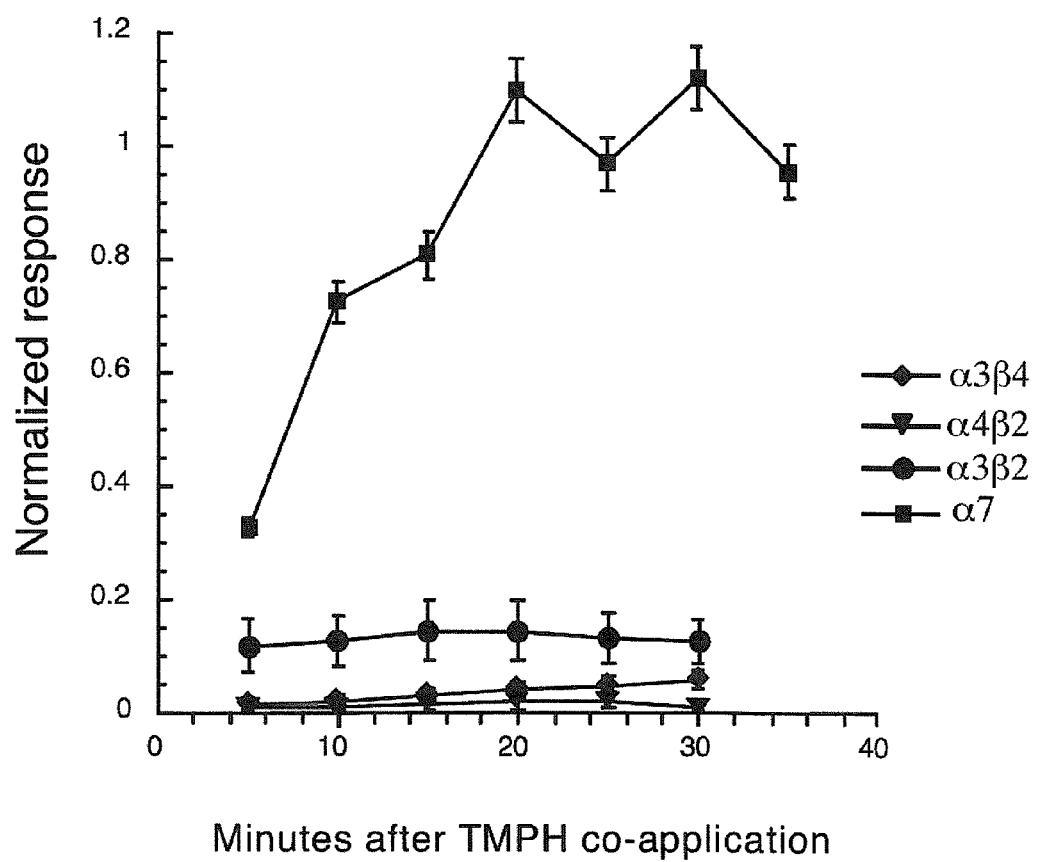
FIG. 6 shows that the recovery of α7 receptors from TMPH-produced inhibition is rapid compared to the recovery of neuronal beta subunit-containing nAChR. ACh and TMPH was co-applied at time 0 to oocytes expressing rat α3β4, α4β2, α3β2, or α7 subunits. Subsequently, control ACh applications were made at 5 min intervals to measure recovery. The control ACh concentrations used were 100 μM, 10 μM, 30 μM, and 300 μM for α3β4, α4β2, α3β2, and α7, respectively. The initial inhibition was produced by the co-application of ACh at the control concentration and 30 μM TMPH, except in the case of the α3β2 receptors, which were inhibited by the co-application of ACh and 3 μM TMPH.

Initial experiments evaluated recovery after only a single 5-minute wash. In order to evaluate the actual rates at which the various nAChR subunit combinations recovered from TMPH-induced inhibition, repeated applications of ACh alone after a single co-application of ACh and TMPH were made. As shown in FIG. 6, the rat α4β2, α3β2, α3β4 showed virtually no detectable recovery over a period of 30 minutes, while α7 receptors were fully recovered after about 15 minutes of wash.

Use-dependence of Inhibition by TMPH

Figure 7A:
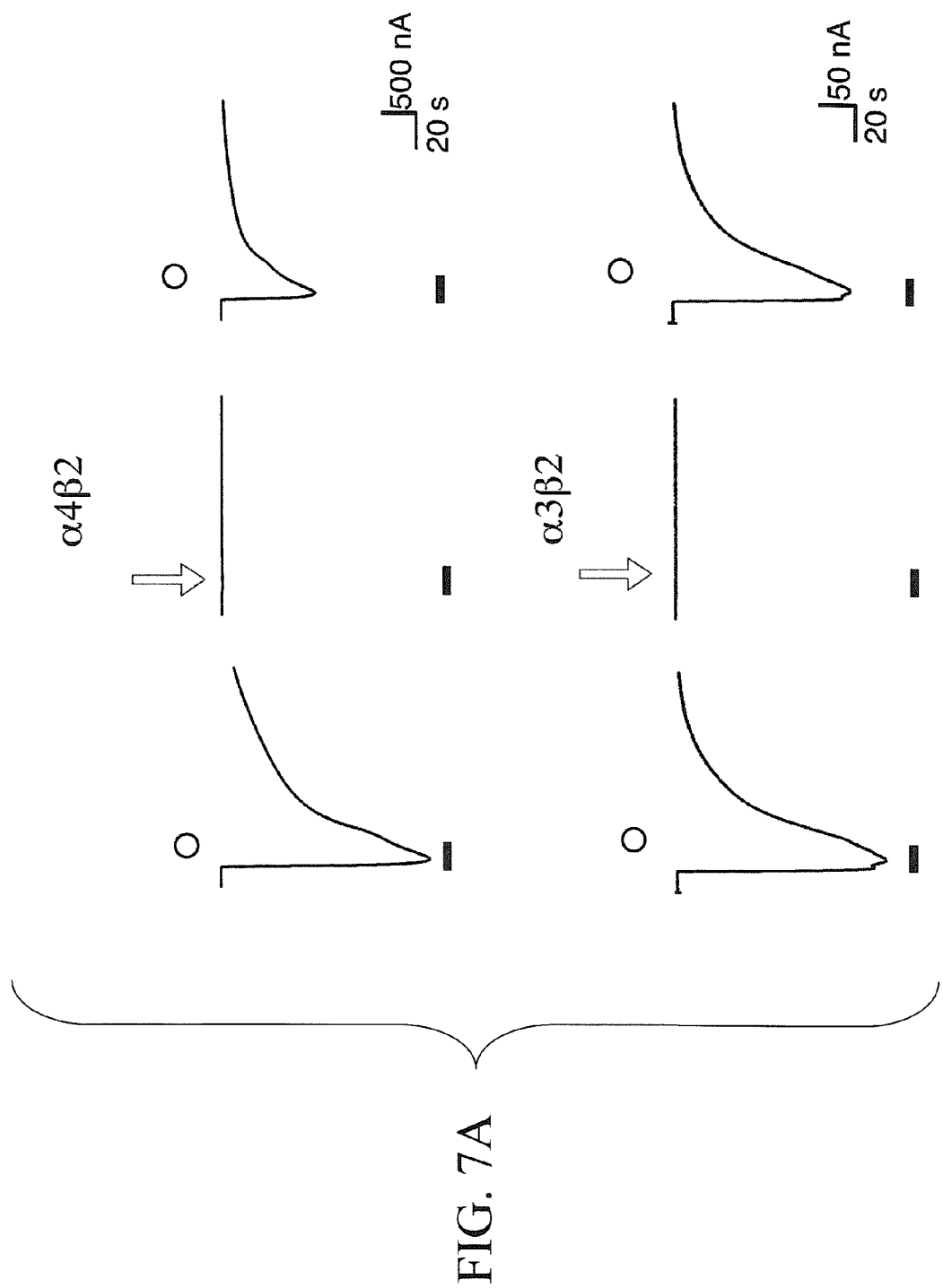
FIGS. 7A-7B show varying amounts of use-independent inhibition of neuronal beta subunit-containing receptors by TMPH.
Figure 7B:
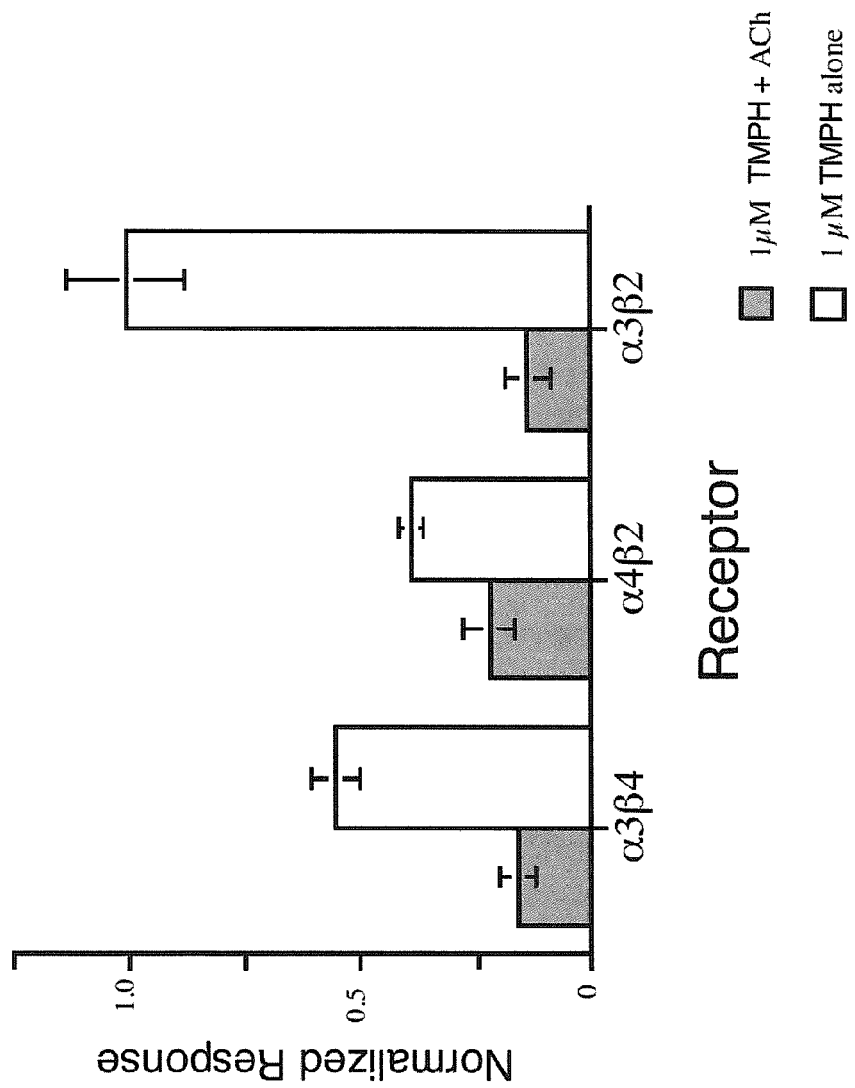

The degree to which inhibition by TMPH was use-dependent was determined by applying 1 μM TMPH alone and comparing the response to a subsequent control ACh application to that obtained after 1 μM TMPH was co-applied with ACh. As shown in FIGS. 7A-7B, the ability of TMPH to inhibit neuronal nAChR when applied in the absence of agonist varied significantly among the pairwise subunit combinations tested, but in all cases was less than when TMPH was co-applied with agonist. Interestingly, while TMPH alone applied to α4β2 receptors was almost as effective as when co-applied with ACh, TMPH alone applied to α3β2 receptors had no detectable effect after the washout period.

Figure 8A:
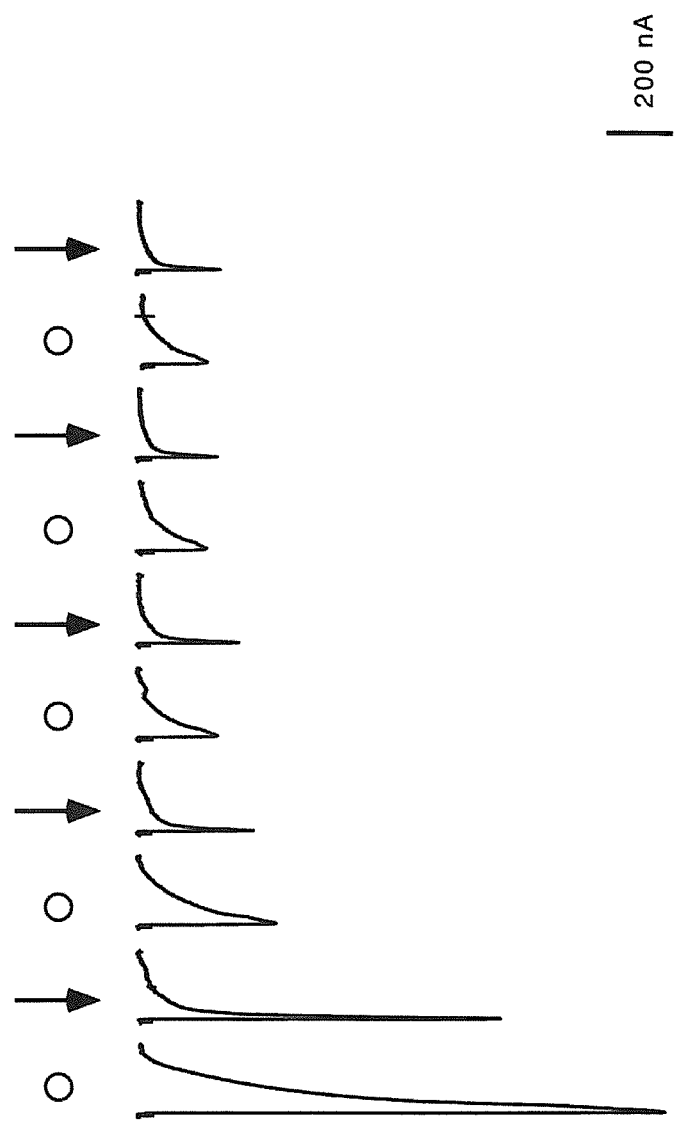
FIGS. 8A-8B show cumulative inhibition by repeated application of TMPH.
Figure 8B:
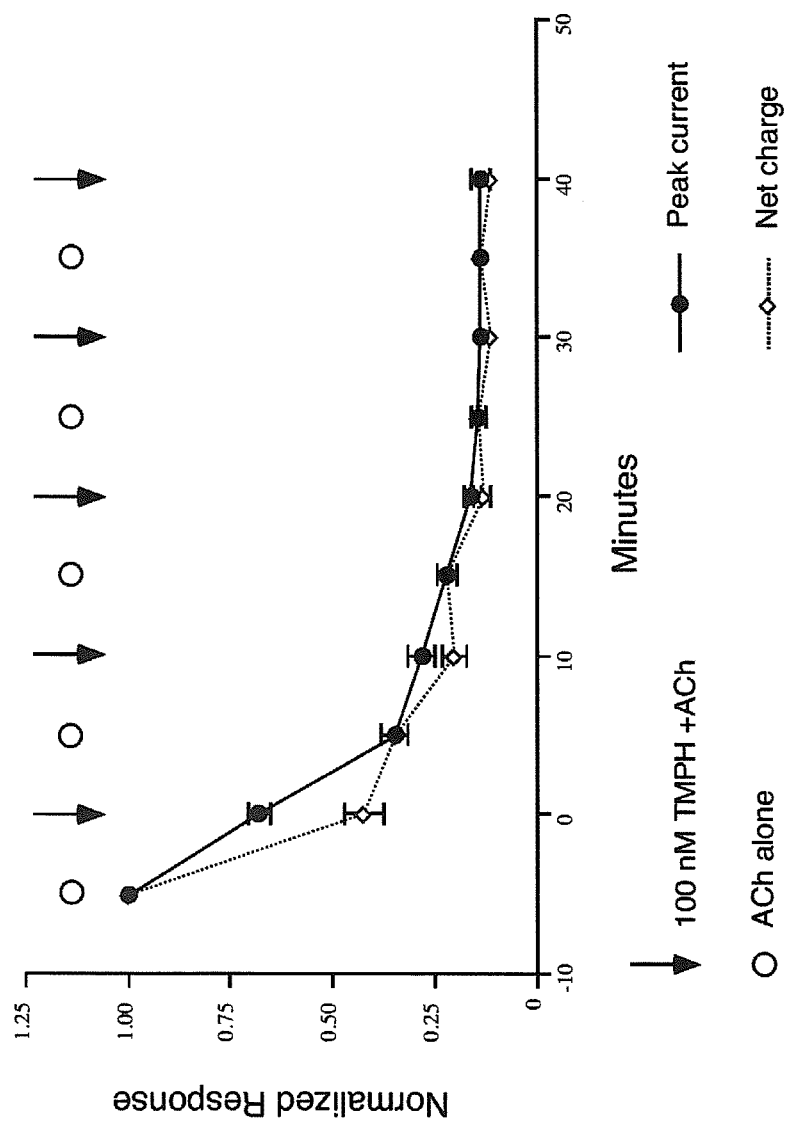

Progressive Inhibition of α4β2 Receptors by Repeated Co-applications of ACh and TMPH Below its $IC_{50}$ Value The $IC_{50}$ values presented in Table 3 were based on the inhibition produced by single co-applications (20 seconds in duration) of ACh and TMPH. Since for the neuronal beta subunit-containing receptors the onset of inhibition is apparently much faster than the reversibility of inhibition, measurements based on single applications of TMPH are likely to underestimate what equilibrium $IC_{50}$s would be. In order to test the hypothesis that repeated applications of TMPH would produce an accumulated inhibition that would be greater than the inhibition produced by a single application, repeated co-applications of ACh and 100 nM TMPH to oocytes expressing α4β2 receptors were carried out. Co-applications of TMPH and ACh were alternated with applications of ACh alone. As shown in FIGS. 8A-8B, repeated co-applications of ACh with 100 nM TMPH (the $IC_{50}$ in single-dose experiments) produced 90% inhibition after 3 applications at 10-minute intervals. Further applications did not produce additional inhibition. Making a corresponding shift in the α4β2 net charge inhibition curve in FIGS. 5A-5C (i.e. so that 100 nM is the $IC_{90}$ rather than the $IC_{50}$) suggests that the equilibrium $IC_{50}$ would be approximately 10 nM.

The Effect of α5 Co-expression with α3β2 Subunits on the Sensitivity to TMPH

As noted above, efforts to connect data obtained from oocyte studies with in vivo data can be complicated by the fact that in vivo nAChR may have more complex subunit composition than the simple pairwise alpha/beta subunit combinations most readily tested in oocytes. Another such subunit that contributes to the complexity of AChRs in vivo is α5, which is not required to co-assemble with other subunits in order for them to function but is likely to be present in some receptor subtypes in vivo (Wang et al. *J. Biol. Chem.*, 1996, 271: 17656-17665; Gerzanich et al. *J. Pharmacol. Exp. Ther.*, 1998, 286:311-320). The hypothesis that the presence of the α5 subunit could modulate the sensitivity of a neuronal nAChR subunit to TMPH was tested. For these experiments, human α3 and β2 subunits were used, which readily form receptors with or without the co-expression of the human α5 subunit. These subunits were selected since the successful inclusion of the α5 subunit produces an easily detectable change in receptor pharmacology, increasing the potency of ACh (Gerzanich et al. *J. Pharmacol. Exp. Ther.*, 1998, 286: 311-320). All batches of oocytes used for these experiments were confirmed to have this predicted effect of α5 expression.

Figure 9A:
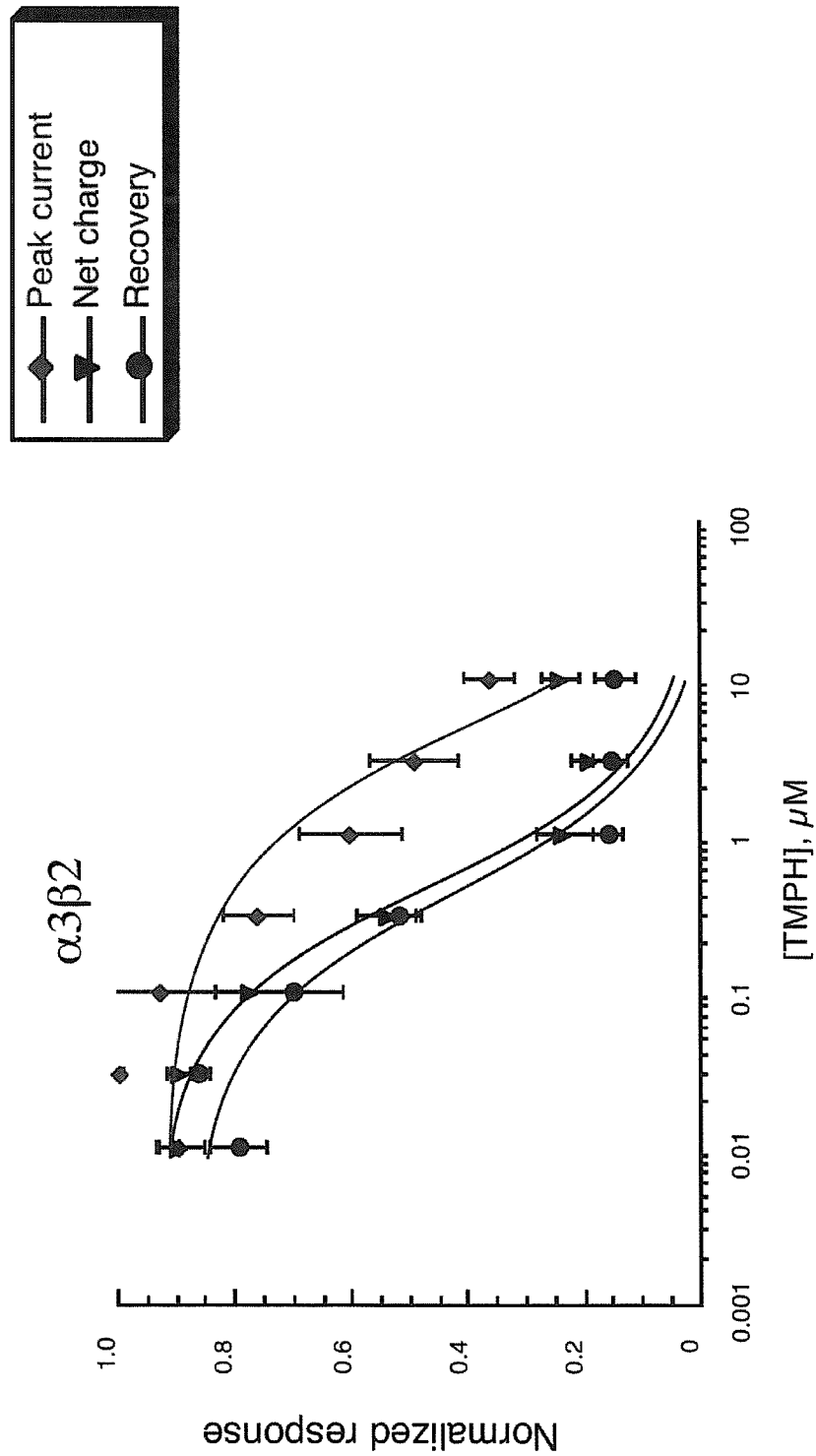
FIGS. 9A-9B show TMPH inhibition of responses obtained from oocytes expressing human neuronal nAChR subunits. Shown are the averaged normalized data (±SEM, n≥4) from oocytes expressing human α3β2 or α3β2α5 subunits (top and bottom, respectively) to the co-application ACh and a range of TMPH concentrations. Three values are plotted in each of the concentration-response curves: (♦) the peak current amplitude of the co-application response, normalized to the peak amplitude of the previous ACh control; (▼) the net charge of the co-application response, normalized to the net charge of the previous ACh control; and (●) the peak current amplitude of the ACh control response obtained after the TMPH/ACh co-application, normalized to the peak amplitude of the previous ACh control. The control ACh concentrations used were 30 μM and 1 μM for α3β2 and α3β2α5 expressing oocytes, respectively.
Figure 9B:
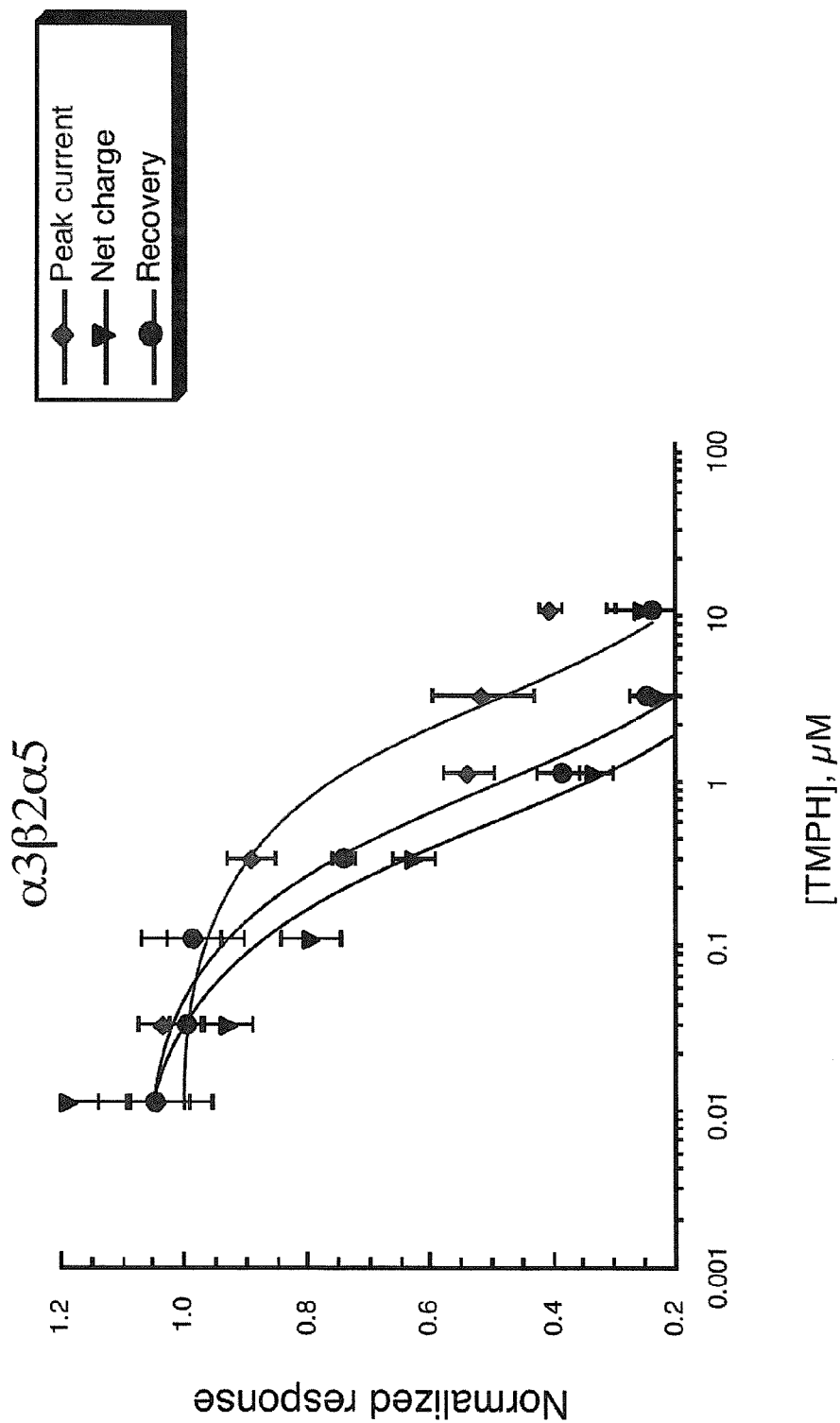
Figure 10A:
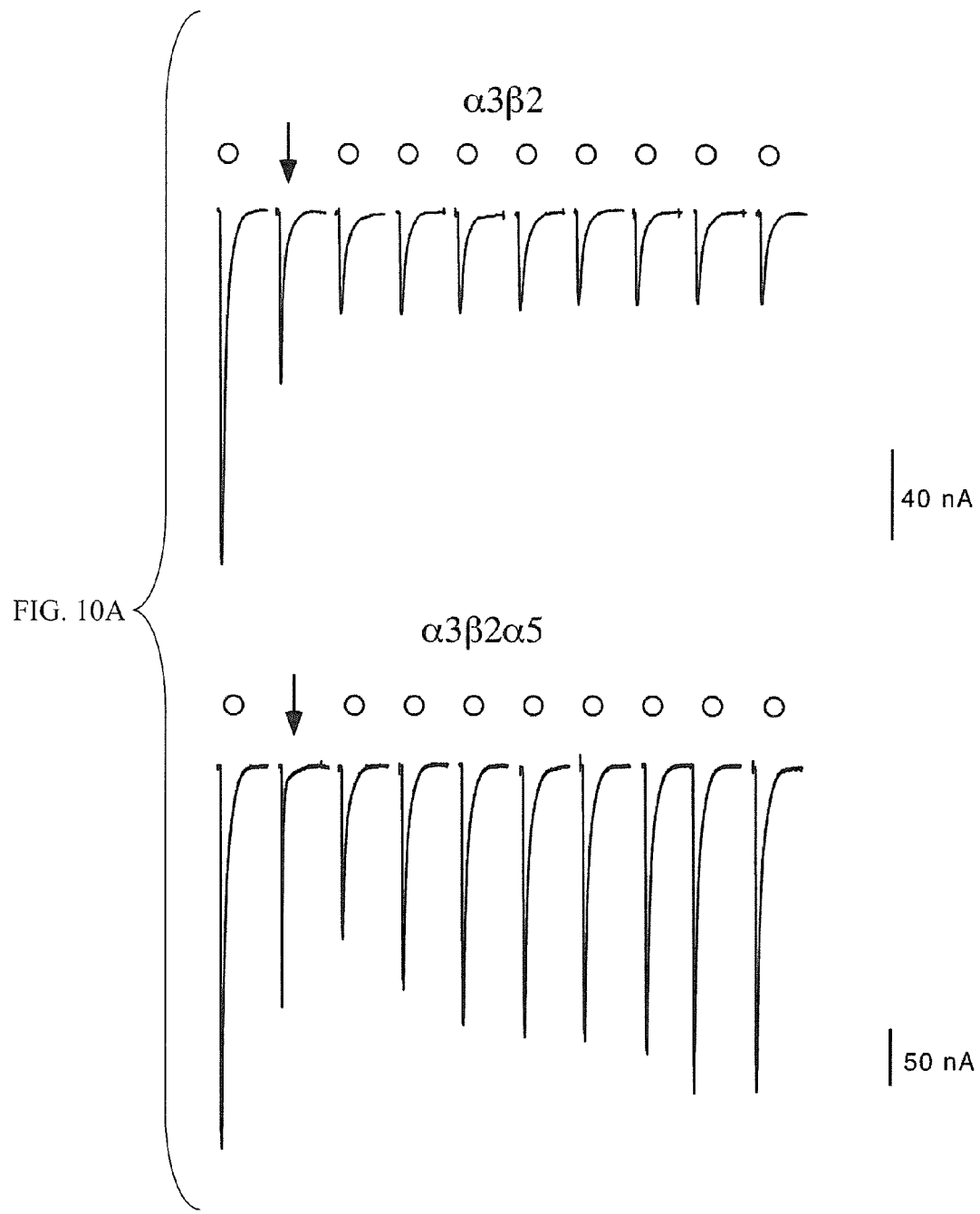
FIGS. 10A-10B show the recovery of human α5-containing α3β2 receptors from TMPH-produced inhibition is rapid compared to the recovery of receptors formed with α3β2 subunits alone.
Figure 10B:
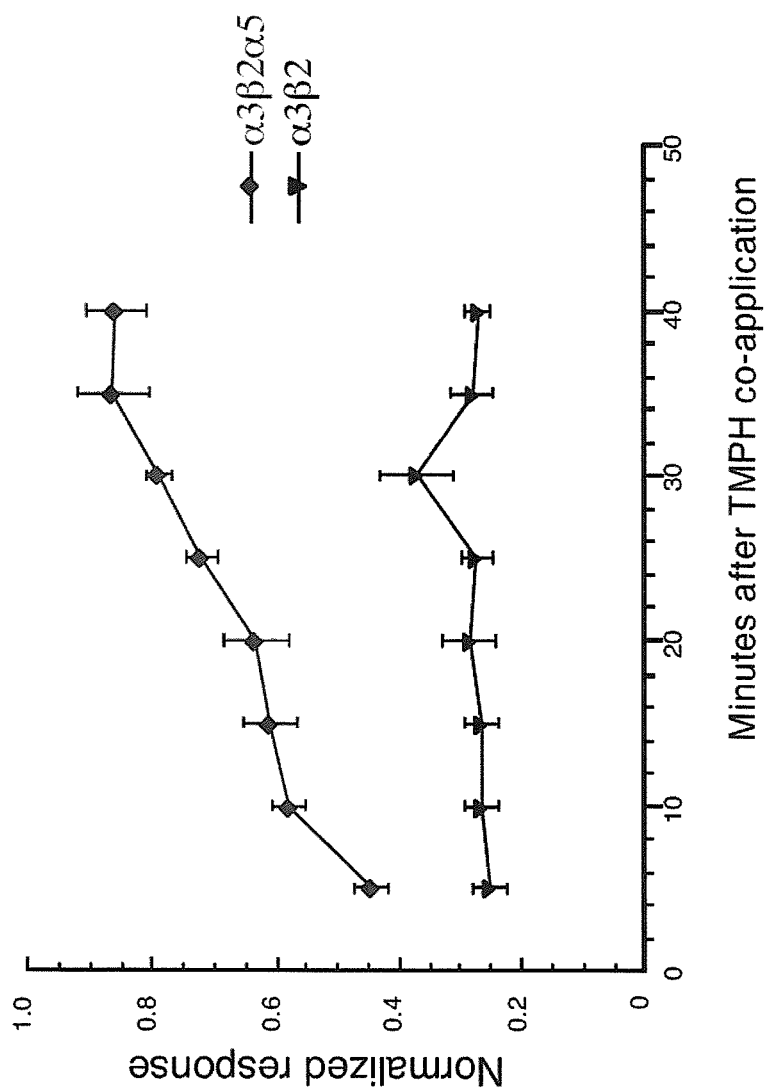

As shown in FIGS. 9A-9B, ACh responses of oocytes expressing human α3β2 and human α3β2α5 showed similar sensitivity to TMPH during the initial co-application. (The IC50 values based on net charge analysis were 460±170 nM and 430±180 nM, respectively.) However, as shown in FIGS. 10A-10B, oocytes expressing α5 along with α3 and β2 showed much faster recovery than those expressing α3 and β2 alone. The responses of oocytes expressing α3β2α5 had a half time of recovery of about 15 minutes, while similar to the oocytes expressing rat α3β2 receptors, those expressing human α3β2 receptors showed no significant recovery over a period of 40 minutes.

Inhibition of Receptors Containing β3 and α6 Subunits.

It has been suggested that in vivo β3 subunits may co-assemble with α6 and possibly α4 and β2 to make receptors that regulate dopamine release (Champtiaux et al. *J Neurosci*, 2003, 23:7820-7829). However, the α6 subunit expresses poorly in oocytes when used in pairwise combinations with beta subunits (Kuryatov et al. *Neuropharmacology*, 2000, 39:2570-2590). Therefore, in initial experiments, in order to evaluate whether the selective sparing of some of nicotine's effects in vivo when TMPH is used as a blocker might be associated with receptors that contain α6 and/or β3, the effects of TMPH on oocytes expressing α3β2β3 and a chimera of α6 and α3 subunits, α6/3 (Dowell et al. *J Neurosci*, 2003, 23:8445-8452) were compared along with β2 and β3. This approach allows systematic evaluation of first the effects of the β3 subunits (by comparing oocytes injected with α3β2β3 to those expressing α3β2 alone), and evaluation of the effects of the α6 extracellular domain (by comparing oocytes injected with the α3/6 chimera in addition to β2 and β3 to those expressing wild-type α3 along with β2 and 3β).

Figure 11A:
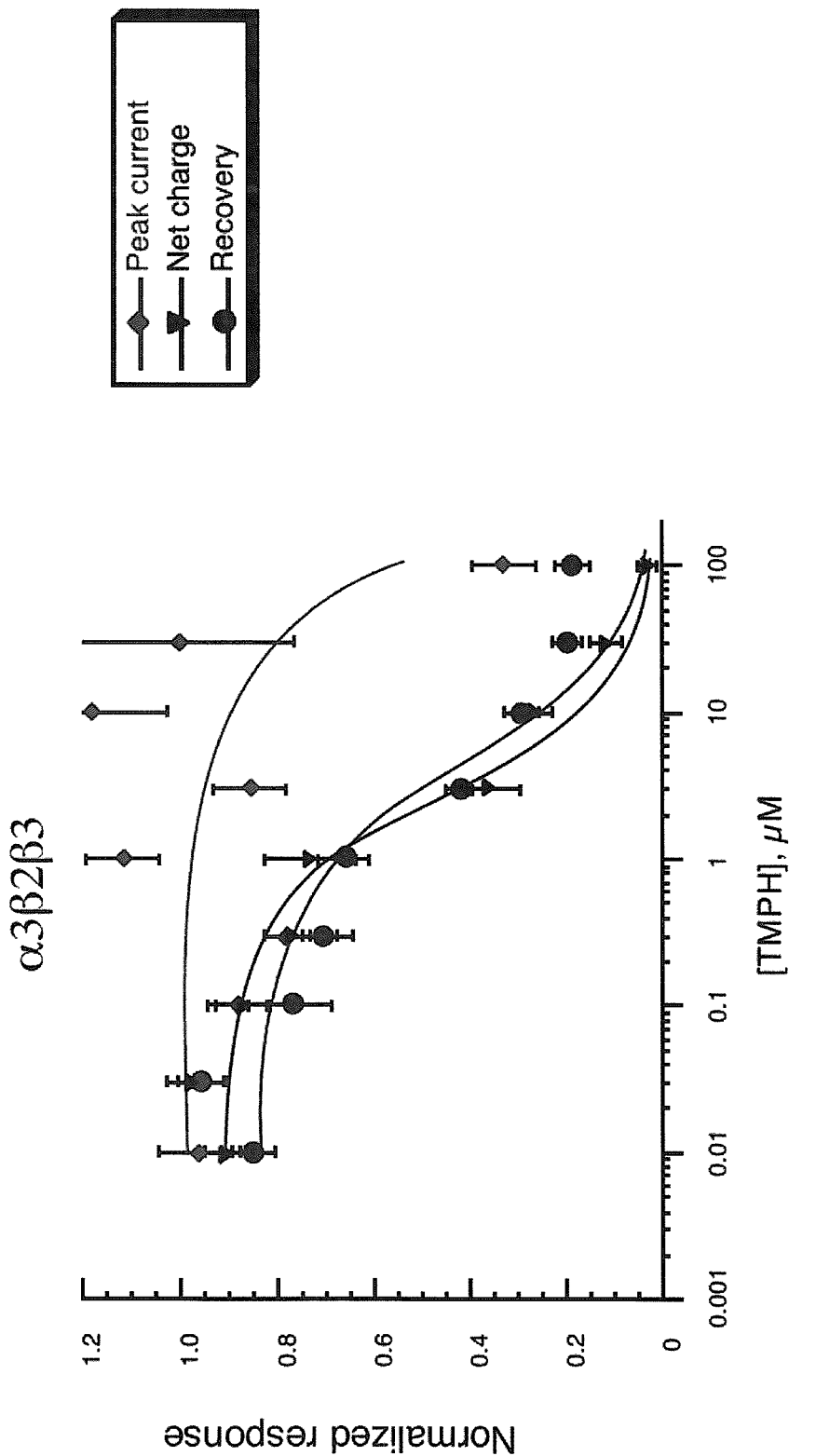
FIGS. 11A-11C show TMPH inhibition of responses obtained from oocytes expressing β3 and chimeric α6/α3 subunits. Shown are the averaged normalized data (±SEM, n≥4) from oocytes expressing human α3β2β3 or α6/3β2β3 subunits (FIGS. 11A and 11B, respectively) to the co-application ACh and a range of TMPH concentrations. Three values are plotted in each of the concentration-response curves: (♦) the peak current amplitude of the co-application response, normalized to the peak amplitude of the previous ACh control; (▼) the net charge of the co-application response, normalized to the net charge of the previous ACh control; and (●) the peak current amplitude of the ACh control response obtained after the TMPH/ACh co-application, normalized to the peak amplitude of the previous ACh control. The control ACh concentration used was 100 μM.
Figure 11B:
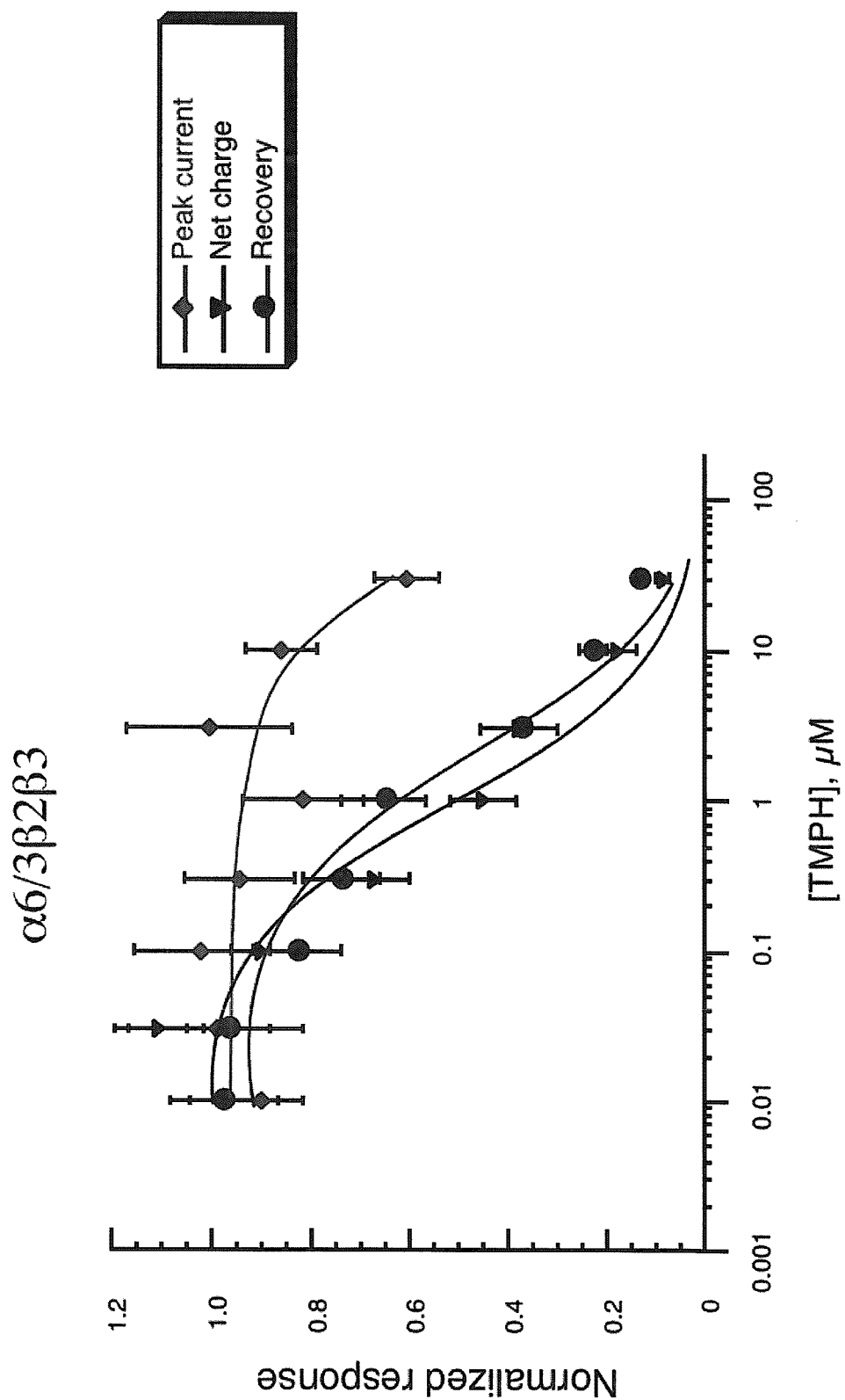
Figure 11C:
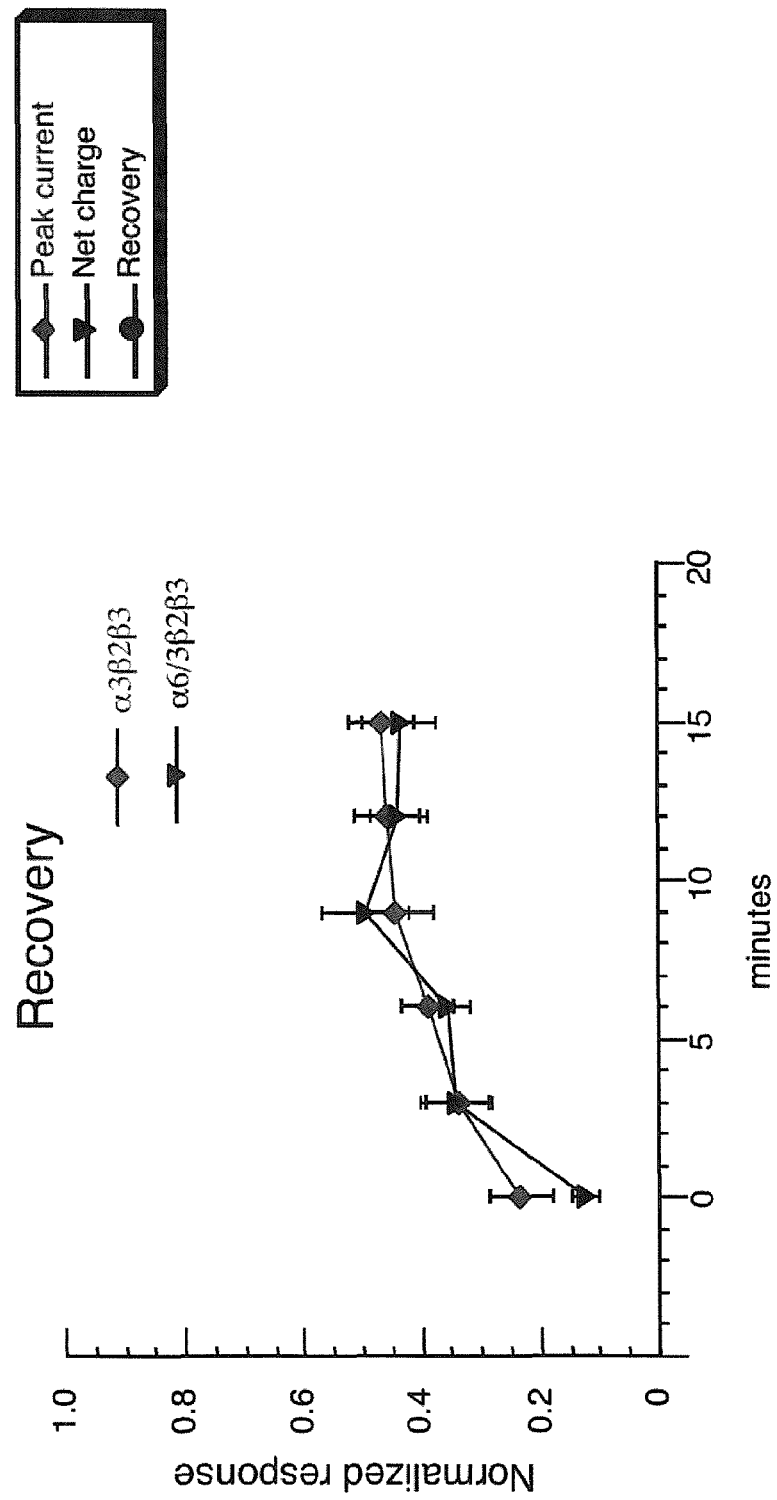

The addition of the β3 subunit along with α3 and β2, had the effect of decreasing sensitivity to an initial application of TMPH (FIG. 9A), such that the 1050 for inhibiting α3β2β3 receptors were at least an order of magnitude high than for the inhibition of α3β2 without β3 (FIGS. 5A-5C and 11A-11C, see also Table 3). The receptors containing the α6/3 chimera in combination with β2 and β3 were not significantly different in their sensitive to TMPH than those expressing α3β2β3 wild-type subunits (FIG. 9B and Table 3). The recovery of β3-containing receptors from TMPH was relatively complex. There was about 50% recovery in the first 10 minutes, but no further recovery after that. This was similar for both α3β2β3 and α6/3β2β3 (FIG. 11C). One possible explanation for this would be if the co-expression of these subunits resulted in mixed populations of receptors, some containing β3 subunits, and showing rapid recovery, and others formed without β3 and showing the nearly irreversible block seen when α3 and β2 are expressed as a pair. This is certainly a likely scenario for combination containing the wild-type α3, and may also be the case for the combination containing the chimera, since in the present inventors' experience there is about a two-fold increase in currents when β3 is co-expressed with β2 and the α6/3 chimera, compared to α6/3 and β2 alone (data not shown).

Figure 12A:
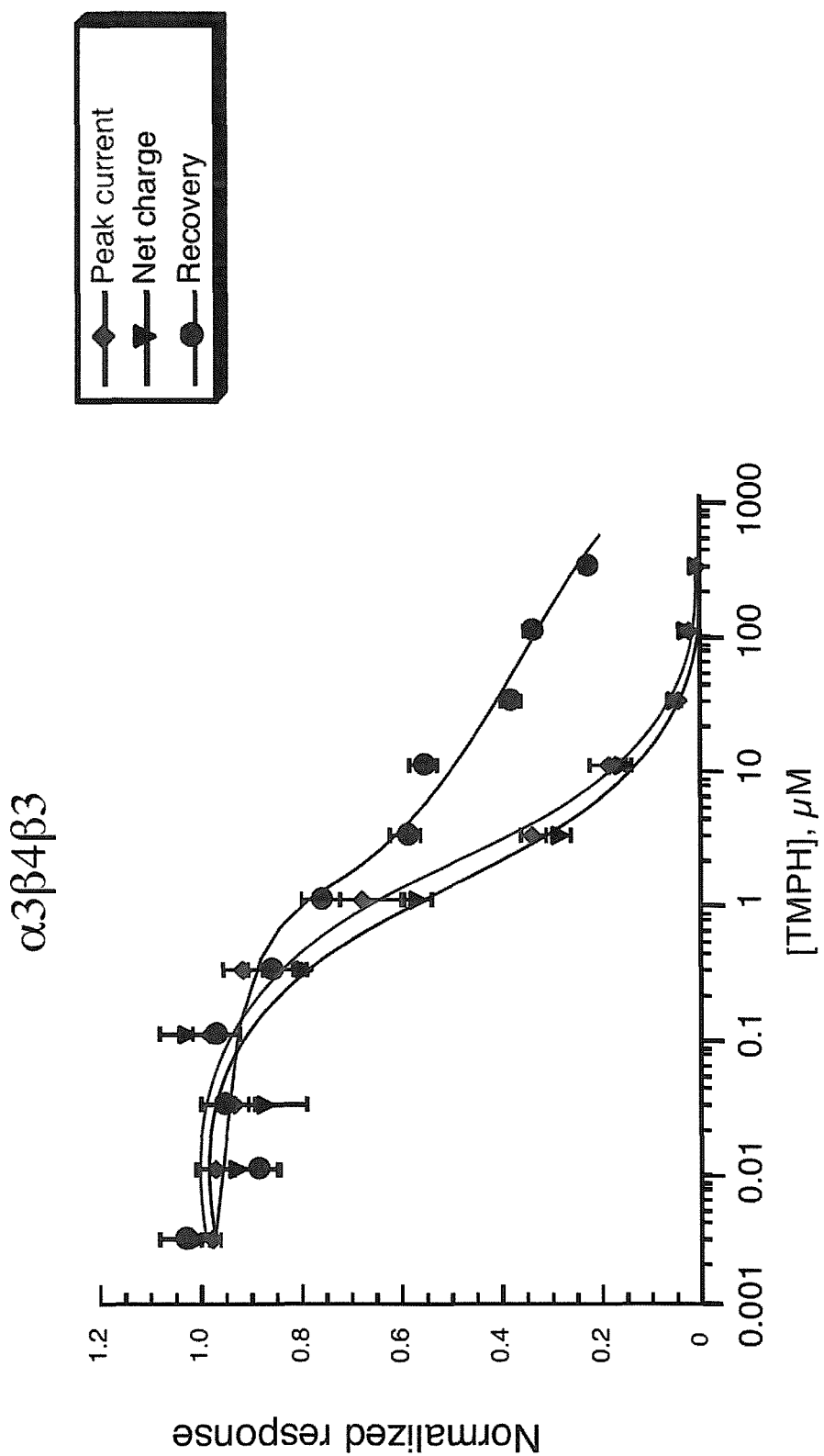
FIGS. 12A-12B show TMPH inhibition of responses obtained from oocytes expressing b4, β3 and either α3 (FIG. 12A) or α6 subunits (FIG. 12B). Shown are the averaged normalized data (±SEM, n≥4) to the co-application 100 μM ACh and a range of TMPH concentrations. Three values are plotted in each of the concentration-response curves: (♦) the peak current amplitude of the co-application response, normalized to the peak amplitude of the previous ACh control; (▼) the net charge of the co-application response, normalized to the net charge of the previous ACh control; and (●) the peak current amplitude of the ACh control response obtained after the TMPH/ACh co-application, normalized to the peak amplitude of the previous ACh control. Note that the recovery data for oocytes expressing α3, β4, and β3 could not be fit to a one site model. The curve fit show is for a 2 site model with approximately 15% fit to an IC$_{50}$ of 1 μM and 85% fit to an IC$_{50}$ of 30 μM.
Figure 12B:
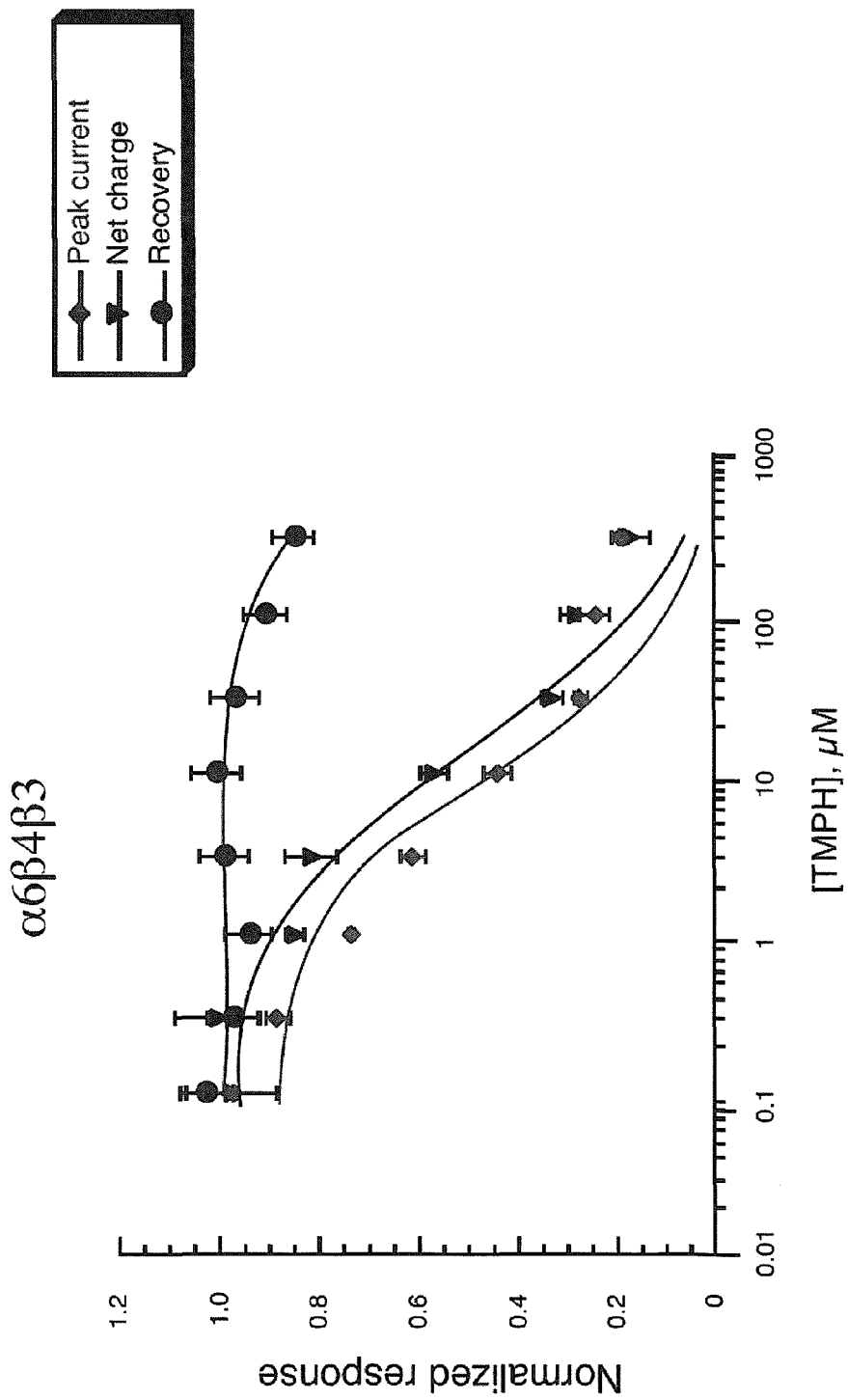

The data in FIGS. 11A-11C suggest that the β3 subunit imparts some resistance to inhibition by TMPH and also that the extracellular domain of α6 had relatively little effect. Therefore, oocytes expressing the complete wild-type α6 subunits were tested. The α6 subunit was co-expressed with β4 and β3 since this is the only α6 combination found to work with any consistency. For these experiments, as a control, the oocytes injected with α6β4β3 were compared to oocytes injected with α3β4β3. As shown in FIGS. 12A-12B, the oocytes injected α6β4β3 showed relatively weak inhibition by TMPH during the co-application of TMPH and inhibitor, with an $IC_{50}$ for the inhibition of net charge nearly an order of magnitude higher than for any other receptor subunit combination tested (Table 3). This reduced sensitivity to TMPH was most likely due to both the α6 and the β3 subunits since α3β4β3 injected oocytes were much less sensitive than those expressing α3β4 alone.

The responses of oocytes expressing α6β4β3 showed essentially full recovery after only a single wash period (FIG. 12B). However, as with the oocytes expressing α3, β2, and β3, it is likely that the cells injected with α3, β4, and β3 had a mixed population of receptor since the recovery data was best fit with a two site model (FIG. 12A).

One of the main objectives of this study was to investigate the antagonistic effect of TMPH on central behavioral effects of nicotine, since this antagonist had not been investigated previously for its blocking effects in vivo. Its antagonistic effects were tested on four different nicotinic responses: antinociception, discriminative cue, locomotor activity and body temperature. It has been shown that only the first two responses are antagonized by TMPH in a dose-related manner. The failure of TMPH to block nicotine-induced motor decrease and hypothermia suggests that it inhibits neuronal nicotinic receptors in a selective manner.

Since the systemic administration of TMPH can inhibit selective effects of nicotine in the CNS, TMPH can apparently pass the blood-brain barrier. The selectivity of TMPH effects in vivo suggests that it may inhibit the effects of nicotine at some nAChR subtypes but not others, and that the nAChR subtypes which mediate the locomotor effects and hypothermic effects of nicotine are less sensitive to TMPH than those which mediate analgetic effects. Based on this study of nAChR expressed in vitro, it is likely that the in vivo effects of TMPH may be due to selective inhibition of neuronal beta subunit-containing receptors that lack the accessory subunits α5, β3, and especially α6 subunit; since the inhibition receptors containing these subunits is relatively week and reversible. Alternatively, α7-type receptors may be some of the TMPH resistant effects.

While with single applications TMPH appears to be more effective for the inhibition of α3β4 receptors than for α4β2 or α3β2 receptors, this may be due to the relative $P_{open}$ values during the co-application responses. That is, for a use-dependent inhibitor, the fractional inhibition increases both as more channels are open and as single channels multiple times (i.e. burst). If, due to their prolonged bursting behavior (Papke and Heinemann *J. Physiol.* (*Lond.*), 1991, 440:95-112), proportionately more α3β4 receptors open or reopen than α3β2 receptors during the co-application response, then the α3β4 receptors will be more likely to be blocked with a given TMPH concentration. Although the sensitivity of α3β4 receptors to TMPH might suggest a high liability for peripheral side effects, this may not be the case since α5 is likely to be present in ganglionic receptors (Vernallis et al. *Neuron*, 1993, 10:451-464).

Compared to mecamylamine, TMPH was equipotent in blocking the effects of nicotine in the mouse hot-plate test and the rat drug discrimination. In contrast, mecamylamine was much more potent in blocking the other effects of nicotine. Nicotine-induced antinociception in the hot-plate test and the nicotine discriminative stimulus were recently reported to be largely mediated by α4β2* subtypes, that is, receptors containing α4, 132 and possibly other subunits such as α6 and β3 (Shoaib et al. *Neuropharmacology*, 2002, 42:530-539; Marubio et al. *Eur J Neurosci*, 2003, 17:1329-1337). The similar potency of TMPH and mecamylamine in blocking these two nicotinic behaviors correlates well with their close potency in blocking expressed α4β2 subtypes (TMPH and mecamylamine $IC_{50}$ (peak) values are 1.4 and 2.5 µM, respectively). The effects on the tail-flick test seem to involve both α4β2* and non-α4β2* receptor subtypes (Marubio et al. *Eur J Neurosci*, 2003, 17:1329-1337). Indeed, contrary to the hot-plate test where a nearly complete loss of the effect was observed, nicotine-induced antinociception in the tail-flick test showed a significant rightward shift in α4 or β2 knock-out mice (Marubio et al. *Eur J Neurosci*, 2003, 17:1329-1337). Compared to mecamylamine, the effects of TMPH on nicotine-induced antinociception in the tail-flick test suggest a lower blockade potency of TMPH on the non-α4β2* receptor subtypes. At this point, it is difficult to predict which nicotinic receptor subtypes are involved in this non-α4β2* component, but it seems that mecamylamine possesses much higher affinity than TMPH to these subtypes. Recent results (Rao et al. *Neuropharmacology*, 1996, 35:393-405; Damaj et al. *J Pharmacol Exp Ther*, 1998, 284:1058-1065), however, indicate little involvement of $α_7$ subtypes in the antinociceptive effects of nicotinic agonists in the tail-flick test.

The lack of TMPH effect on nicotine-induced hypomotility and hypothermia is very interesting and further indicates the in vivo selectivity of TMPH for blocking different nicotinic receptors. The depressing effect of nicotine on locomotor activity in mice involves α5 (Salas et al. *Mol Pharmacol*, 2003, 63:1059-1066) and 132 subunits (Tritto et al. *Nicotine Tob Res*, 2004, 6:145-158), but not α4 (Salas et al. *Mol Pharmacol*, 2003, 63:1059-1066), α7 (Tritto et al. *Nicotine Tob Res*, 2004, 6:145-158) and β4 subunits as reported in recent studies using knock-out mice of these various subunits. Similarly, nicotine-induced hypothermia involves β2 but not α7 subunits (Tritto et al. *Nicotine Tob Res*, 2004, 6:145-158). The lack of effects of TMPH seems to correlate well with its relatively weak blocking of α3α5β2 receptors. Mecamylamine and TMPH block β2-containing receptors with similar potency, so these results suggest that the greater inhibitory activity of mecamylamine on nicotine-induced antinociception may also be due to an involvement of α5-containing receptor subtypes. Although little data are available on nicotine-induced hypothermia, the lack of TMPH's effects may possibly involve similar receptor mechanisms.

In conclusion, the results suggest that drug therapies for the inhibition of CNS nicotinic receptors may be developed with greater selectivity than previously appreciated. While more selective antagonists such as MLA are known, these generally work poorly with systemic administration. Mecamylamine has previously been proposed for adjunct therapy for Tourette's syndrome (Sanberg et al. *Lancet,* 1998, 352:705-706) and smoking cessation (Rose et al. *Clin. Pharinacol. Ther.,* 1994, 56:86-99). The characterization of selective antagonists such as TMPH may lead the way to the development of better therapies for these, and potentially other, neuropsychiatric indications based on a more limited profile of side effects. For example, in regard to smoking cessation, it is particularly interesting to note that TMPH blocks nicotine discrimination with a potency equal to or greater than that of mecamylamine. However, while the concentrations of mecamylamine required to block drug discrimination would profoundly block potentially desirable antinociception mechanisms (as measured by tail-flick, Table 2), concentrations of TMPH effective at blocking drug discrimination leave the effects of nicotinic receptors on tail flick responses largely intact. In addition to the potential therapeutic significance of TMPH, this drug may also prove to be a valuable tool to combine with selective agonists and knockout animals to further unravel the mystery of how neuronal nicotinic receptors play a role in brain function.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A composition comprising 2,2,6,6-tetramethylpiperidin-4-yl heptanoate, or a pharmaceutically acceptable salt thereof, and a nicotine acetylcholine receptor agonist, wherein said agonist is nicotine.

2. The composition of claim 1, wherein said composition further comprises a pharmaceutically acceptable carrier.

3. The composition of claim 1, wherein said composition is incorporated into a sustained release preparation.

4. The composition of claim 1, wherein said nicotine is provided in the form of a nicotine patch for administration transdermally.

5. The composition of claim 1, wherein the composition is provided in a form for subcutaneous administration.

6. A method for treating Tourette's syndrome or another tic disorder in a person or animal, comprising administering an effective amount of a composition comprising 2,2,6,6-tetramethylpiperidin-4-yl heptanoate, or a pharmaceutically acceptable salt thereof, and a nicotine acetylcholine receptor agonist to the person or animal, wherein said agonist is nicotine.

7. The method of claim 6, wherein said composition further comprises a pharmaceutically acceptable carrier.

8. The method of claim 6, wherein said nicotine is provided in the form of a nicotine patch for administration transdermally.

9. The method of claim 6, wherein the composition is provided in a form for subcutaneous administration.

10. A method of treating nicotine addiction in a person or animal, comprising administering an effective amount of a composition comprising 2,2,6,6-tetramethylpiperidin-4-yl heptanoate, or a pharmaceutically acceptable salt thereof, and a nicotine acetylcholine receptor agonist to the person or animal, wherein said agonist is nicotine.

11. The method of claim 10, wherein said composition further comprises a pharmaceutically acceptable carrier.

12. The method of claim 10, wherein said composition is incorporated into a sustained release preparation.

13. The method of claim 10, wherein said composition further comprises a pharmacologically active compound for treating nicotine addiction.

14. The method of claim 10, wherein said nicotine is provided in the form of a nicotine patch for administration transdermally.

* * * * *

UNITED STATES PATENT AND TRADEMARK OFFICE
CERTIFICATE OF CORRECTION

PATENT NO. : 8,980,923 B2
APPLICATION NO. : 13/526076
DATED : March 17, 2015
INVENTOR(S) : Roger L. Papke et al.

Page 1 of 1

It is certified that error appears in the above-identified patent and that said Letters Patent is hereby corrected as shown below:

In the specification

Column 3,
Line 59, "and (33 subunits" should read --and β3 subunits--.

Column 10,
Line 10, "foiins" should read --forms--.

Column 15,
Lines 28-29, "(6.2 mmol/kg" should read --(6.2 µmol/kg--.

Column 17,
Line 21, "50 nl" should read --50 nl--.

Column 20,
Line 17, "Ooces" should read --oocytes--.

Column 23,
Line 3, "1050" should read --1C50--.

Column 24,
Line 30, "132 and possibly" should read --β2 and possibly--.
Line 60, "132 subunits" should read --β2 subunits--.

Column 25,
Line 16, "*Pharinacol.*" should read --*Pharmacol.*--.

Signed and Sealed this
Eighth Day of March, 2016

Michelle K. Lee
*Director of the United States Patent and Trademark Office*